(12) United States Patent
Light et al.

(10) Patent No.: US 7,622,122 B2
(45) Date of Patent: Nov. 24, 2009

(54) METHODS OF USING NOVEL TISSUE FACTOR TARGETED THROMBOMODULIN FUSION PROTEINS AS ANTICOAGULANTS

(75) Inventors: David Bruce Light, San Mateo, CA (US); Kirk McLean, Oakland, CA (US)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 11/766,160

(22) Filed: Jun. 21, 2007

(65) Prior Publication Data

US 2008/0020965 A1 Jan. 24, 2008

Related U.S. Application Data

(62) Division of application No. 10/427,805, filed on Apr. 30, 2003, now Pat. No. 7,250,168.

(60) Provisional application No. 60/376,566, filed on May 1, 2002.

(51) Int. Cl.
*A61K 39/00* (2006.01)
(52) U.S. Cl. .............. 424/192.1; 424/134.1; 424/143.1; 424/185.1
(58) Field of Classification Search ........................ None
See application file for complete search history.

(56) References Cited

U.S. PATENT DOCUMENTS

| | | | |
|---|---|---|---|
| 4,208,479 | A | 6/1980 | Zuk |
| 4,912,207 | A | 3/1990 | Majerus |
| 5,256,770 | A | 10/1993 | Glaser |
| 5,298,599 | A | 3/1994 | Rezaie |
| 5,466,668 | A | 11/1995 | Glaser |
| 5,506,134 | A | 4/1996 | Soule |
| 5,574,007 | A | 11/1996 | Zushi |
| 5,589,173 | A | 12/1996 | O'Brien |
| 5,827,824 | A | 10/1998 | Light |
| 5,843,442 | A | 12/1998 | Soule |
| 5,863,760 | A | 1/1999 | Light |
| 5,874,407 | A | 2/1999 | Kelley |
| 5,916,874 | A | 6/1999 | Fujiwara |
| 5,986,065 | A | 11/1999 | Wong |
| 6,063,763 | A | 5/2000 | Light |
| 6,274,142 | B1 | 8/2001 | O'Brien |
| 6,555,319 | B2 | 4/2003 | Wong |
| 6,632,791 | B1 | 10/2003 | Light |
| 2006/0166284 | A1 | 7/2006 | Light |
| 2008/0019985 | A1 | 1/2008 | Light |

FOREIGN PATENT DOCUMENTS

| | | |
|---|---|---|
| WO | WO 88/07543 | 10/1988 |
| WO | WO 88/09811 | 12/1988 |
| WO | WO 90/10081 | 9/1990 |
| WO | WO 98/40408 | 9/1998 |
| WO | WO 01/70984 | 9/2001 |
| WO | WO 01/98352 | 12/2001 |
| WO | WO 03/057911 | 5/2003 |

OTHER PUBLICATIONS

Bajzar et al., J Biol Chem. Jul. 12, 1996;271(28):16603-8.*
Koutsi et al., Int J Biochem Cell Biol. 2008;40(9):1669-73. Epub Jul. 18, 2007.*
Price et al. Anaesthesia 2004, 59:483-492.*
Fay et al., Blood Reviews 2005, 19:15-27.*
Chapman et al., "Therapeutic antibody fragments with prolonged in vivo half-lives," *Nature Biotechnology 17*, 780-83, 1999.
Harlow et al., *Antibodies, A Laboratory Manual*, Harlow & Lane, eds., Cold Spring Harbor Laboratory, 1988, pp. 340-341.
Heyman et al., "Carbohydrate Chains on IgG2b: A Requirement for Efficient Feedback Immunosuppression," *J. Immunol. 134*, 4018-23, 1985.
Janeway et al., *Immunobiology*, $3^{rd}$ ed., Garland Publishin Inc., 1997, pp. 3:7-3:9.
Amit et al., 1986, *Science 233*, 747-53.
Rudikoff et al., *Proc. Natl. Acad. Sci. USA 79*, 1979-83, 1982.
Stedman's Medical dictionary, $27^{th}$ ed., 2000, definition of synergism, downloaded Oct. 26, 2006 from thomsonhc.com, 2 pages.
On-line Medical dictionary definition of synergy, downloaded Oct. 26, 2006 from cancerweb.ncl.ac.uk, 1 page.
Skolnick et al., *Trends in Biotechnology 18*, 34-39, 2000.
Whisstock et al., *Quarterly Review of Biophysics 36*, 307-40, 2003.
Fuentes-Prior et al., "Structural Basis for the anticoagulant Activity of the Thrombin-thrombomodulin Complex," *Letters to Nature 404*, 518-25, Mar. 30, 2000.
Clarke et al., The Short Loop Between epidermal Growth Factor-like Domains 4 and 5 is Critical for Human Thrombomodulin Function, *J. Biol. Chem. 268*, 6309-15, Mar. 25, 1993.
Hall et al., "Thrombin Interacts with Thrombomodulin, Protein C, and Thrombin-activatable Fibrinolysis Inhibitor via Specific and Distinct Domains," *J. Biol. Chem. 274*, 22510-16, Sep. 3, 1999.
Nagashima et al., "Alanine-scanning Mutagenesis of the epidermal Growth Factor-like Domains of Human Thrombomodulin Identifies Critical Residues for its Cofactor Activity," *J. Biol. Chem. 268*, 2888-92, Feb. 5, 1993.
Wang et al., "Elements of the Primary Structure of thrombomodulin Required for Efficient Thrombin-activable Fibrinolysis Inhibitor Activation," *J. Biol. Chem. 275*, 22942-47, Jul. 28, 2000.

(Continued)

*Primary Examiner*—Michael Szperka
(74) *Attorney, Agent, or Firm*—Banner & Witcoff, Ltd.

(57) ABSTRACT

This invention relates to novel fusion proteins which are comprised of a targeting protein that binds tissue factor (TF), which is operably linked to the thrombomodulin (TM) EGF456 domain alone or in combination with at least one other TM domain selected from the group consisting of the N-terminal hydrophobic region domain, the EGF123 domain, the interdomain loop between EGF3 and EGF4, and the O-glycosylated Ser/Thr-rich domain, or analogs, fragments, derivatives or variants thereof. The fusion protein binds at the site of injury and prevents the initiation of thrombosis. The fusion protein can be used to treat a variety of thrombotic conditions including but not limited to deep vein thrombosis, disseminated intravascular coagulation, and acute coronary syndrome.

5 Claims, 11 Drawing Sheets

OTHER PUBLICATIONS

Figure 1:
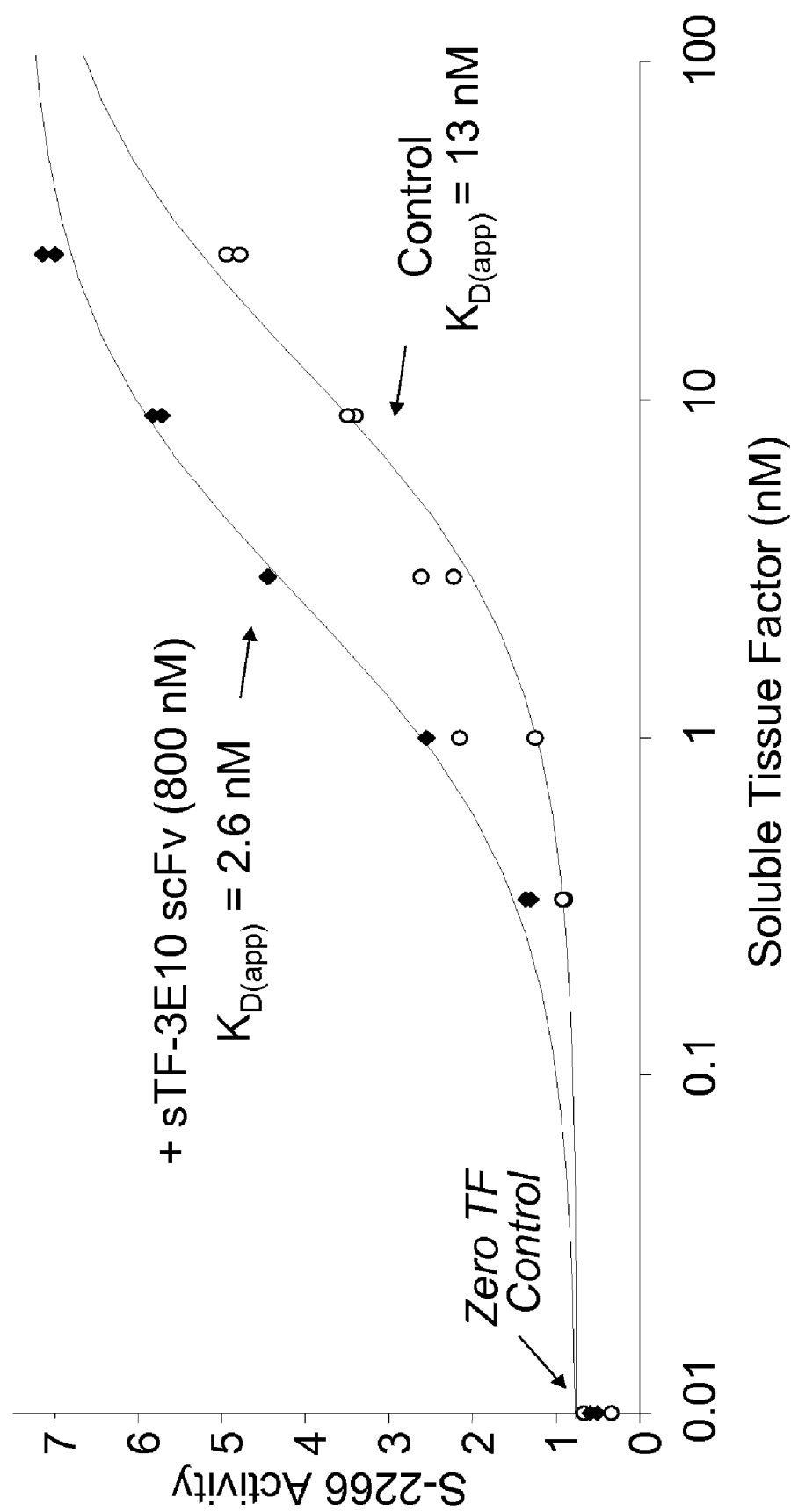

Bitonti et al., Pulmonary Delivery of an Erythropoietin Fc Fusion Protein in Non-human Primates Through an Immunoglobulin Transport Pathway, *Proc. Natl. Acad. Sci. USA 101*, 9763-68, Jun. 29, 2004.

Dong et al., "P-selectin-targeting of the Fibrin Selective Thrombolytic Desmodus Rotundus Salivary Plasminogen Activator α1," *Thrombl Haemost*. 92, 956-65, 2004.

Adams et al., "Thrombin-cofactor Interactions: structural Insights into Regulatory Mechanisms," *Arteriosclerosis, Thrombosis, and Vascular Biology 26*, 1738-45, May 25, 2006.

Dahlback et al., "Blood Coagulation," *The Lancet 355*, 1627-32, May 6, 2000.

Faelber et al., "The 1.85 Å Resolution Crystal Structures of Tissue factor in Complex with Humanized Fab D3h44 and of Free Humanized Fab D3h44: Revisiting the Solvation of antigen combining Sites," *Mol. Biol*. 313, 83-97, 2001.

Haber et al., "Antibody Targeting as a Thrombolytic strategy," *Ann. NY Acad. Sci*. 667, 365-81, 1992.

Moons et al., "Tissue Factor and Coronary Artery Disease," *Cardiovascular Res*. 53, 313-25, 2002.

Gresele et al., "Novel Approaches to the Treatment of Thrombosis," *Tresnds Pharmacol. Sci*. 23, 25-32, 2002.

Esmon, "Regulation of Blood Coagulation," *Biochim. Biophys. Acta 1477*, 349-60, 2000.

Esmon, "The Roles of Protein C and Thrombomodulin in the Regulation of Blood Coagulation," *Biol. chem*. 264, 4743-4846, 1989.

\* cited by examiner

METHODS OF USING NOVEL TISSUE FACTOR TARGETED THROMBOMODULIN FUSION PROTEINS AS ANTICOAGULANTS

This application is a continuation of U.S. application Ser. No. 10/427,805, filed Apr. 30, 2003, which claims the benefit of U.S. Provisional Application Ser. No. 60/376,566, filed May 1, 2002, both of which are incorporated herein in full by reference.

BACKGROUND

Maintaining the proper balance between procoagulant and anticoagulant activity within blood vessels is essential for normal hemostasis (Davie, E. W. et al. (1991) *Biochemistry*, 30(43):10363-10370). Perturbing the balance toward coagulation leads to thrombosis, which can cause heart attack, stroke, pulmonary embolism, and venous thrombosis. There is a need for more effective and safer anticoagulants for the treatment of specific thrombotic disorders.

Tissue factor ("TF") is a transmembrane glycoprotein that is the major initiator of the coagulation cascade (Nemerson, Y. (1995) *Thromb. Haemost.* 74(1):180-184). Under normal physiological conditions active TF is not in contact with blood. During vascular injury, exposure to blood of sub-endothelial TF and collagen leads to activation of coagulation factors and platelets and subsequently to hemostatic plug formation. The inappropriate induction of TF expression in a variety of clinical settings can lead to life threatening thrombosis and/or contribute to pathological complications. TF exposure following plaque rupture is believed to be responsible for thrombotic occlusion leading to acute myocardial infarction and stroke. In these settings, proinflammatory signaling pathways activated by coagulation factors also contribute to edema formation and increased infarct size. Vascular injury associated with angioplasty leads to upregulation of TF on SMC's which is believed to induce cell signaling pathways associated with restenosis. TF overexpression in cancer and gram-negative sepsis leads to life threatening thrombosis and activation of inflammatory pathways.

The factor VIIa ("FVIIa")/TF complex is involved in the pathogenic mechanism in a variety of thrombotic diseases and the circulating level of TF is a risk factor for certain patients. FVIIa and TF play unique roles in vascular injury in maintaining hemostasis and initiating thrombosis. TF is expressed in the adventitia normally, but is upregulated and expressed inappropriately in the media and neointima in vascular disease. TF expression in atherosclerotic plaques is increased and shielded from the blood by a thin fibrous cap that may rupture to expose TF. Surgical interventions such as balloon angioplasty, stenting, or endarterectomy damage the vessel wall and expose underlying TF. In the atherosclerotic, lipid-rich, thin-walled plaque, spontaneous rupture or endothelial erosion leads to TF exposure and thrombosis, resulting in unstable angina and myocardial infarction. TF can circulate in cell derived microparticles and circulating TF levels are elevated in unstable angina suggesting that this circulating TF may contribute to thrombus formation (Soejima, H. et al. (1999) *Circulation* 99(22):2908-2913). Often cancer is associated with a hypercoagulable state attributed to overexpression of TF on tumor cells. This predisposes the patient to deep vein thrombosis, pulmonary embolism and low grade disseminated intravascular coagulation ("DIC"). DIC results in microvascular fibrin deposition contributing to multi-organ failure. Results from acute arterial injury models of thrombosis indicate that protein based inhibitors of FVIIa/TF, such as active site inhibited factor VIIa ("FVIIai") and tissue factor pathway inhibitor ("TFPI"), are effective antithrombotics with less bleeding compared to thrombin and factor Xa ("FXa") inhibitors. In addition, FVIIa/TF inhibition is superior to other anticoagulants (e.g., heparin, FXa inhibitors) in preventing neointimal thickening and vascular stenosis following balloon injury (Jang, Y. et al. (1995) *Circulation* 92(10):3041-3050).

Thrombomodulin ("TM") is a transmembrane glycoprotein that has anticoagulant properties and is predominantly expressed on the lumenal surface of endothelial cells lining blood vessels (Esmon, N. L. et al. (1982) *J. Biol. Chem.* 257(2):859-864; Salem, H. H. et al. (1983) *J. Biol. Chem.* 259(19):12246-12251). The mature, full length TM is a 557 amino acid residue modular protein composed of 5 structural domains: an N-terminal, hydrophobic region (residues 1-226); a cysteine-rich region (residues 226-462); a O-glycosylated Ser/Thr-rich region (residues 463-497); a hydrophobic transmembrane region (residues 498-521); and a C-terminal cytoplasmic tail (residues 522-557).

The cysteine-rich region includes six repeated structures homologous to epidermal growth factor ("EGF") precursor, called EGF-like, EGF-homology or EGF domains. The cysteine-rich region can be further divided into 3 domains: the EGF-like repeats 1, 2 and 3 ("EGF123", residues 226-344), the interdomain loop between EGF3 and EGF4 (residues 345-349), and the EGF-like domains 4, 5 and 6 ("EGF456", residues 350-462). The function of EGF456 is to mediate thrombin binding and protein C activation. One study has suggested that the fifth and sixth EGF-like repeats ("EGF5", residues 390-407, and "EGF6", residues 427-462, respectively) have the capacity to bind thrombin (Kurosawa, S. et al. (1988) *J. Biol. Chem.* 263(13):5993-5996); another suggests the EGF456 domain is sufficient to act as cofactor for thrombin-mediated protein C activating activity (Zushi, M. et al. (1989) *J. Biol. Chem.* 264(18):10351-10353). The Ser/Thr-rich domain enhances EGF456-mediated thrombin binding. The third EGF-like repeat ("EGF3", residues 311-344) is required for the activation of thrombin-activatable fibrinolysis inhibitor ("TAFI"). Several point mutants in EGF3 have been described that interfere with the activation of TAFI (Wang, W. et al. (2000) *J. Biol. Chem.* 275(30):22942-22947). The thrombin/TM complex converts protein C to activated protein C ("APC"), which in turn degrades factors Va and VIIIa, thereby preventing further thrombin generation. Therefore, TM functions as a molecular switch converting thrombin from a procoagulant to an anticoagulant.

The $K_m$ of protein C for the thrombin/TM complex is reduced 10-fold when TM is localized to a membrane surface (Esmon, C. T. (1995) *FASEB J.* 9(10):946-955). The concentration of protein C in blood (0.065 μM) is significantly below the reported $K_m$ (5 μM) for the soluble TM/thrombin complex, therefore establishing that TM on the procoagulant membrane surface will result in a marked local enhancement of the rate of protein C generation.

TM inhibits thrombosis by a different mechanism from heparin or its derivatives. Heparin is a cofactor for antithrombin III and inhibits both FXa and thrombin through an antithrombin III-dependent mechanism. Thrombus-bound thrombin is protected from the action of antithrombin III, which limits the antithrombotic efficacy of heparin or low molecular weight heparin ("LMWH") on preexisting clots. This explains the failure of heparin or LMWH to inhibit thrombus growth triggered by clot-bound thrombin or prothrombinase in non-human primate studies. In contrast, recombinant TM attenuates clot induced thrombin generation and fibrin formation in a dose dependent manner (Mohri, M. et al. (1998) *Thromb. Haemost.* 80(6):925-929). The inhibitory effect of TM is abolished by anti-protein C antibody. Inhibiting clot-bound procoagulant activity is clinically relevant because clot-bound procoagulant activity results in more rapid thrombus growth and ultimately in vascular occlusion or thromboembolic complications. Inhibition of thrombus growth allows the endogenous fibrinolytic systems to remove clots more rapidly and completely. In addition, TM is also expected to be more effective than heparin in pathological conditions where plasma antithrombin is depleted, such as DIC. While both TM and heparin inhibit platelet and fibrinogen consumption in experimental DIC, only TM was effective when antithrombin III levels were depleted.

SUMMARY OF THE INVENTION

The present invention provides novel fusion proteins, which act as anticoagulants, and comprise a targeting protein, that interacts with either tissue factor ("TF") or the factor VIIa/tissue factor ("FVIIa/TF") complex, which is operably linked to the thrombomodulin ("TM") EGF456 domain alone or in combination with at least one other TM domain selected from the group consisting of the N-terminal hydrophobic region domain, the EGF123 domain, the interdomain loop between EGF3 and EGF4, and the O-glycosylated Ser/Thr-rich domain, or analogs, fragments, derivatives or variants thereof.

The anticoagulant fusion protein of this invention targets and binds TF or the FVIIa/TF complex at the site of injury, localizing TM to the injury site, and thus preventing thrombus formation and thereby performing more effectively as an anticoagulant compared to either a soluble anti-TF antibody or soluble TM or fragments of TM. The fusion protein is more effective than low molecular weight heparin ("LMWH") in the treatment of certain diseases including but not limited to sepsis, disseminated intravascular coagulation, ischaemic stroke, deep vein thrombosis, acute coronary syndromes, thrombotic complications following angioplasty, and coagulopathy in advanced cancer. Further, the fusion protein has use in microvascular surgery, skin and vein grafts and organ transplants.

In another aspect, the invention provides pharmaceutical compositions including the subject fusion proteins.

In another aspect, the invention provides for a method of protecting a patient against thrombus formation comprising administering a therapeutically effective amount of the fusion protein to said patient, and thereby inhibiting the generation of thrombin without directly affecting other coagulation parameters such as the activation and aggregation of platelets.

In another aspect, the invention relates to a method for preventing and treating deep vein thrombosis ("DVT") or disseminated intravascular coagulation ("DIC") or acute coronary syndrome or cancer with evidence of coagulopathy in a patient comprising administering a therapeutically effective amount of the fusion protein to said patient.

In another aspect, the invention relates to a method for regulating the inflammatory response in a patient comprising administering a therapeutically effective amount of the fusion protein to said patient.

In yet another aspect, the fusion protein of the invention can be used to form a non-thrombogenic coating on the surface of medical devices contacting blood.

In another aspect, the invention relates to a kit comprising a fusion protein comprising a targeting protein, that binds TF or the FVIIA/TF complex, and TM domains. Alternately, the kit may comprise DNA sequences encoding the fusion protein components.

Also disclosed are methods of making the fusion proteins of the invention, both recombinant and synthetic.

DESCRIPTION OF THE FIGURES

FIG. 1. Binding of scFv(TF)3e10 to sTF increases the apparent affinity of sTF for FVIIa. The sTF/FVIIa activation assay was performed as described under Example 5 entitled "sTF/FVIIa activation assay" using 2 nM FVIIa in the presence and absence of 800 nM scFv(TF)3e10. The sTF was titrated into the assay and the rate of cleavage of the chromogenic substrate (S-2266) was determined. The $K_D$ apparent for sTF was calculated using a standard 4-parameter fit.

FIG. 2. Measurement of binding affinity of scFv(TF)3e10 for sTF. The sTF/FVIIa assay was as described under Example 5 entitled "sTF/FVIIa activation assay" using 3 nM sTF and 2 nM FVIIa. The concentration of sTF used was below the $K_D$ for binding to FVIIa. Binding of the scFv(TF) 3e10 antibody reduced the $K_D$ of sTF for binding to FVIIa, leading to increased formation of the sTF/FVIIa complex and, therefore, the rate of cleavage of the chromogenic substrate S2266. ScFv(TF)3e10 was added at increasing concentrations and the increased rate of reaction was used to determine the $K_D$ apparent of the antibody for sTF using a standard 4-parameter fit.

FIG. 3. Microcalorimetry analysis shows scFv(TF)3e10 has a 20-fold higher affinity for the sTF/FVIIa complex than sTF alone. Isothermal titration calorimetry was performed using a MicroCal VP-ITC instrument. The sTF/FVIIa complex was preformed by adding a 2.3 fold molar excess of FVIIai to sTF. Size exclusion chromatography was used to verify that the sTF was completely complexed. For determination of the antibody affinity for the complex, 1.2 μM sTF/VIIa complex was added to the microcalorimeter cell and 65 μM scFv(TF)3e10 antibody was added to the syringe. For determination of the antibody affinity for sTF alone, 10 μM sTF was added to the cell and 141 μM scFv(TF)3e10 was added to the syringe. Data analysis was done using MicroCal Origin software. The data was fit to a single binding site.

FIG. 4. scFv(TF)3e10 dose dependently inhibits the FX activation assay. The details of this assay are described under Example 5 entitled "Factor X activation assay". The $IC_{50}$ represents the dose required to reach 50% maximum inhibition.

FIG. 5. The fusion protein more potently inhibits coagulation than TF antibody or TMi456 alone. A prothrombin time (PT) assay was performed to compare the fusion protein with TF antibody or TMi456 alone. An appropriate volume of concentrated inhibitor, either TF antibody (scFv(TF)3e10), TMi456, or fusion (scFv(TF)3e10-TMi456), was added to 100 μl of recombinant human thromboplastin (Ortho Recombiplastin). Approximately 2 minutes later 100 μl reconstituted human plasma was added. Coagulation time was determined in a Haemoliance Coagulometer. Dose response curves were generated for each inhibitor and then regression analysis was used to calculate the concentration (in nM) necessary for a two-fold extension of the clotting time.

FIG. 6. The fusion protein retains full cofactor activity for the activation of protein C. The assay described under Example 5 entitled "Protein C activation assay (chromogenic)" contained 20 μl TM sample, either TMi456, which contains the EGF domains 4-6 and the interdomain loop between EGF3 and EGF4, or fusion (scFv(TF)3e10-TMi456), 20 μl 1.5 μM protein C, and 20 μl 3 nM alpha thrombin. Activation was allowed to proceed for 1 hour. The activation phase was stopped by adding 20 μl 0.16 u/ml hirudin. 100 μl of 1 mM S2266 was then added and the A405 determined every 10 seconds for 30 minutes. The rate of reaction is dependent on the amount of activated protein C generated. Data is expressed in mOD/min.

Figure 7:
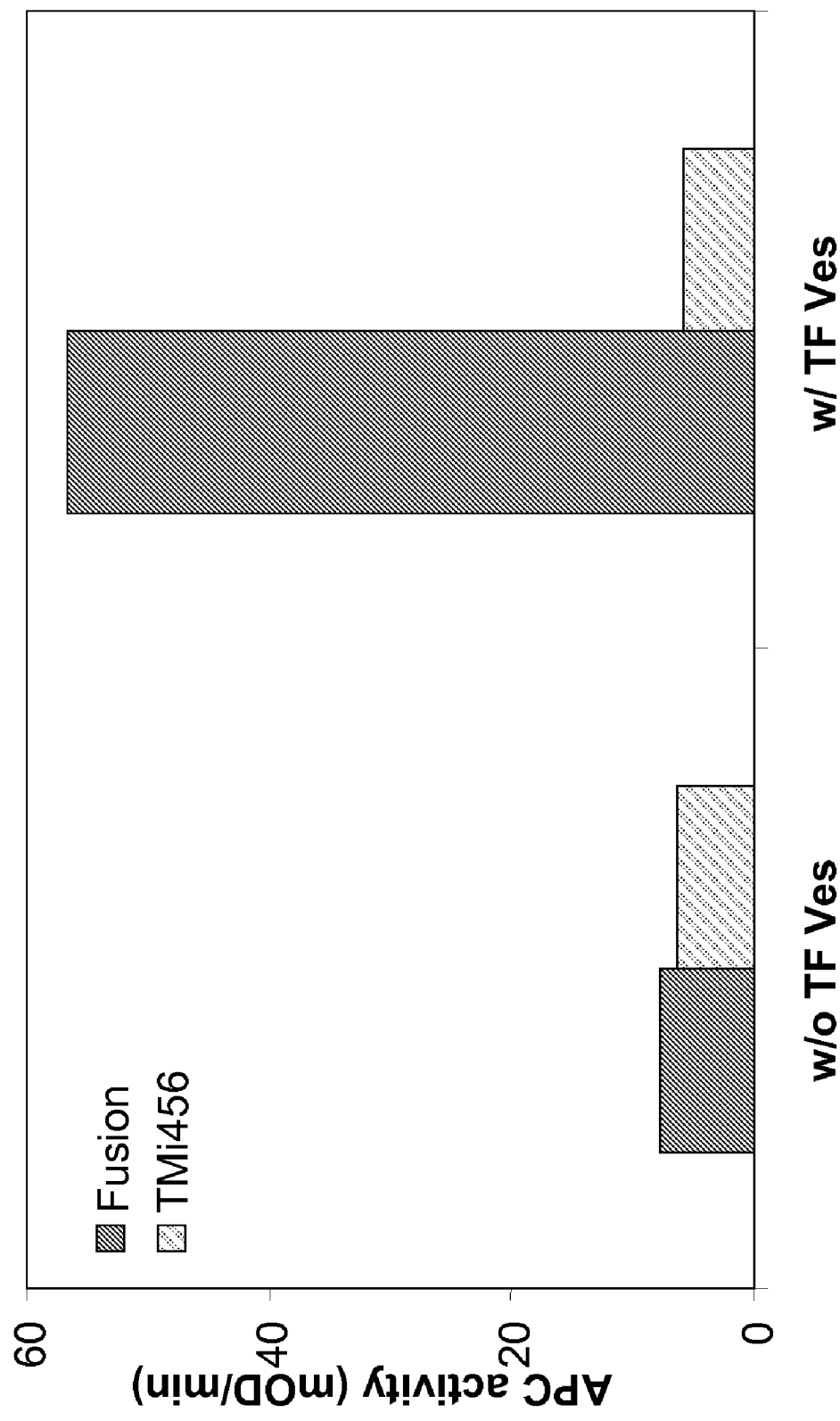

FIG. 7. The rate of protein C activation by the fusion protein is enhanced on TF-containing phospholipid surfaces. The rate of protein C activation by TMi456 is not affected by the addition of TF vesicles. The assay described under Example 5 entitled "Protein C activation assay (on TF-rich surface)" contained 20 μl TM sample, either TMi456 or fusion (scFv(TF)3e10-TMi456), 20 μl of 1.5 μM protein C, 20 μl of 3 nM alpha thrombin, and 20 μl of buffer or TF vesicles (Innovin, human recombinant TF, 4× normal concentration for PT). Activation was allowed to proceed for 1 hour. The activation phase was stopped by adding 20 μl 0.16 u/ml hirudin. 100 μl of 1 mM S2266 was then added and the A405 determined every 10 seconds for 30 minutes. The rate of reaction is dependent on the amount of activated protein C generated. Data is expressed in mOD/min.

Figure 8:
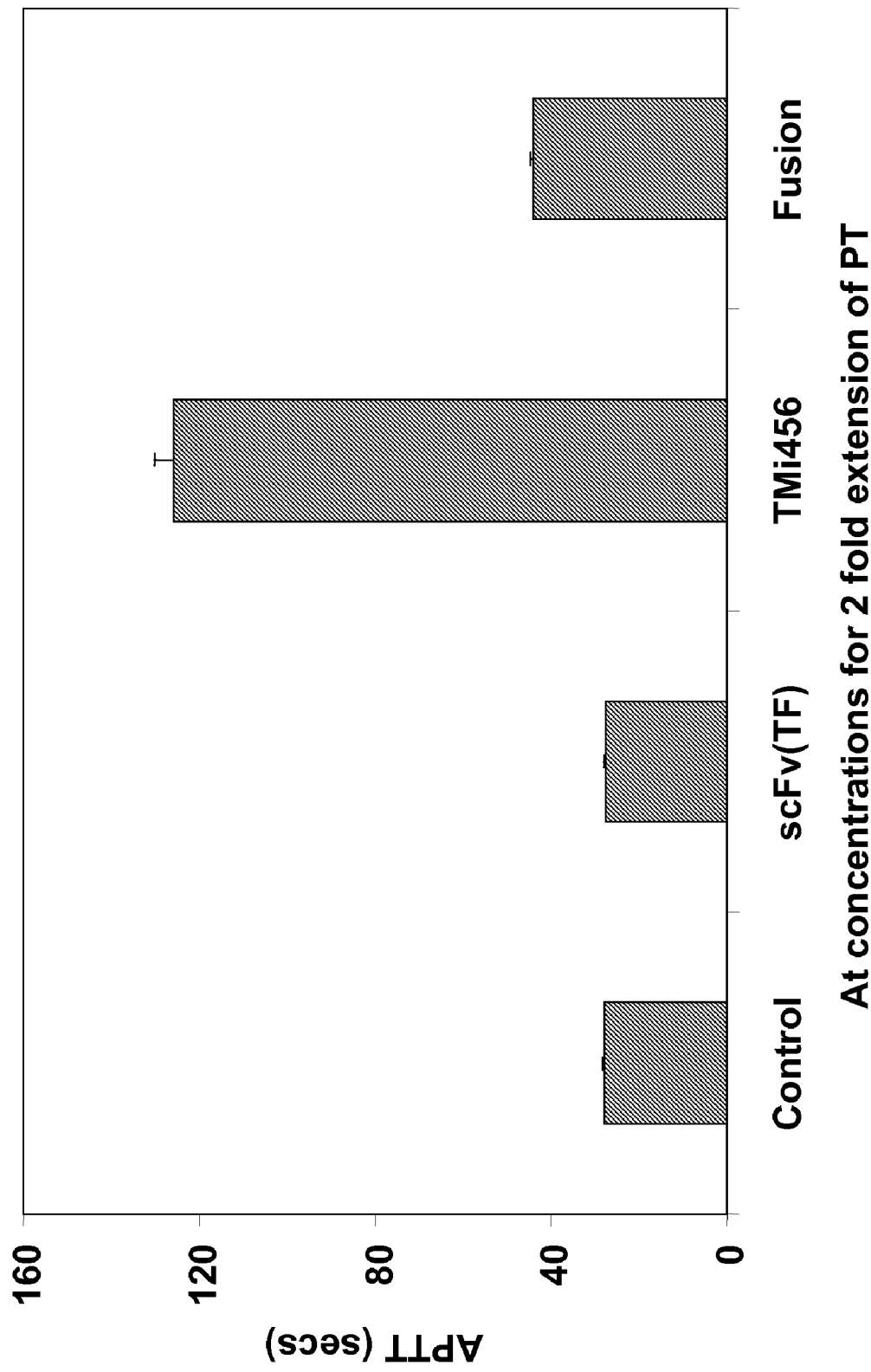

FIG. 8. The fusion protein shows greater specificity for TF-induced coagulation than TMi456. The activated partial thromboplastin time (APTT) assay is sensitive to inhibitors of the intrinsic and central pathways of coagulation. Coagulation that occurs in this assay is independent of TF. The inhibitors, either TF antibody (scFv(TF)3e10), TMi456, or fusion (scFv(TF)3e10-TMi456), were diluted into 50 μl reconstituted human plasma to a final concentration that gave a two-fold extension in the PT assay. The coagulometer then added 50 μl of APTT (Alexin HS) reagent and 50 μl of $CaCl_2$ reagent (0.02 mol/L) and determined the clotting time in seconds.

Figure 9:
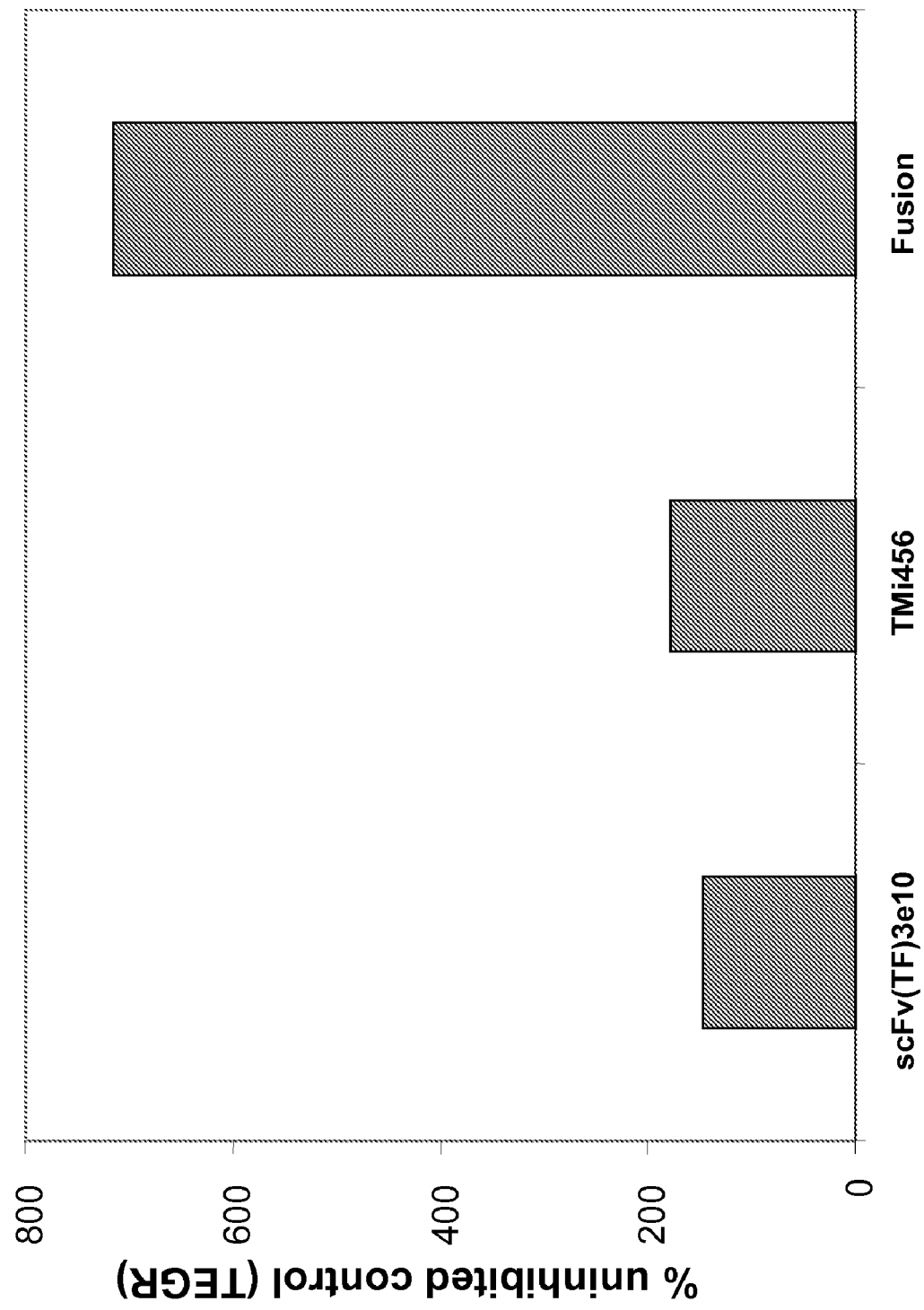

FIG. 9. The fusion protein more potently inhibits TF-induced whole blood coagulation than either of its components alone. Whole blood coagulation was analyzed using a Haemoscope Thromboelastogragh (TEG) analyzer. To citrated whole blood, 120 nM of TF antibody (scFv(TF)3e10), TMi456, or fusion (scFv(TF)3e10-TMi456) was added along with 10 μl of a thromboplastin reagent (1:64 dilution) and 20 μl of 0.2M $CaCl_2$. The R-value (time to initial fibrin formation) was obtained for each sample. This value was then converted to a % uninhibited control R-value.

Figure 10:
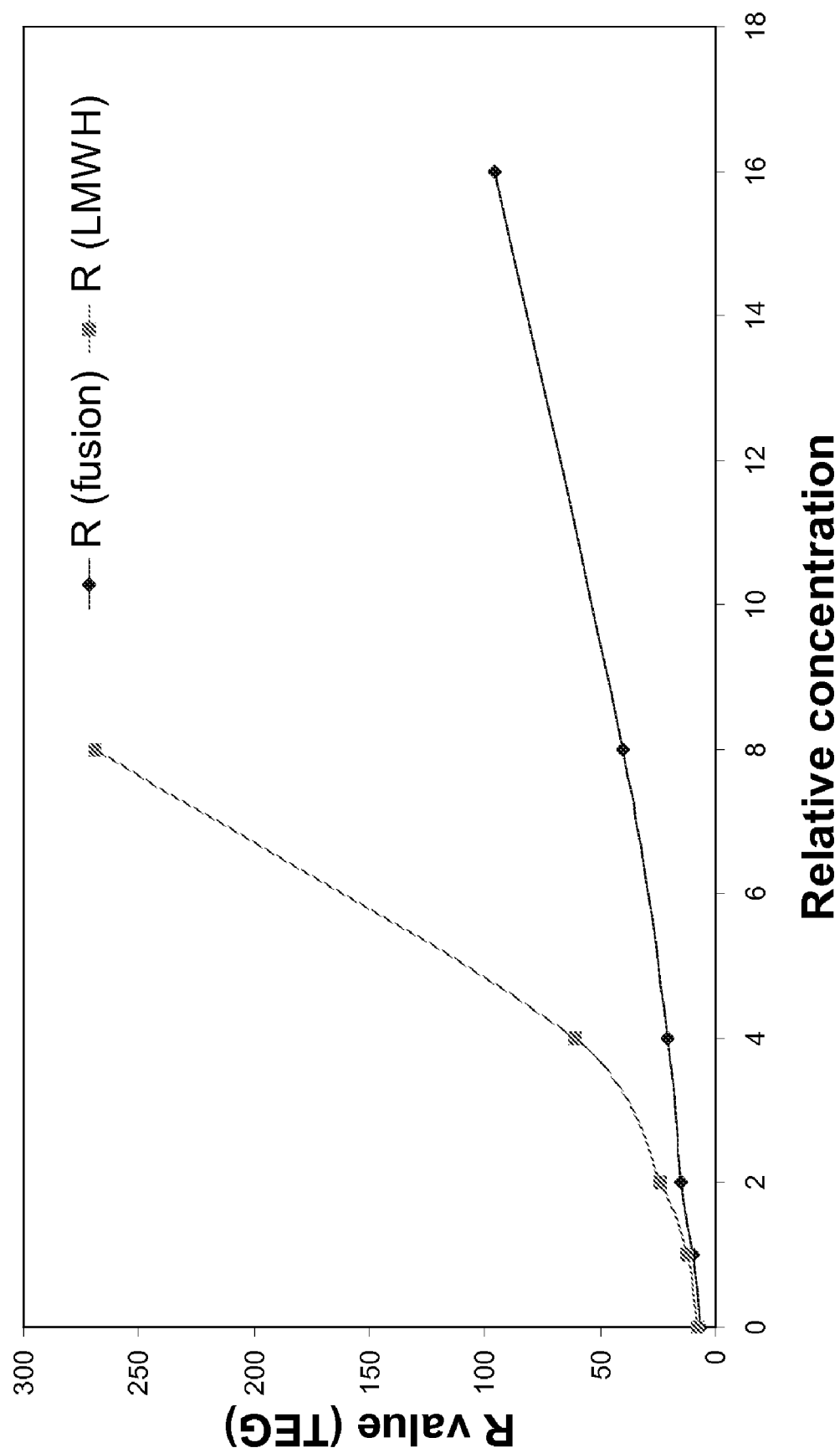

FIG. 10. The fusion protein shows a more predictable dose response than LMWH in a whole blood coagulation assay (TEG). To citrated whole blood, increasing concentrations (15 nM starting and increased by 2× increments) of fusion (scFv(TF)3e10-TMi456), or increasing concentrations (0.15 u/ml starting and increased by 2×) of enoxaparin (LMWH), were added along with 10 μl of a thromboplastin reagent (1:64 dilution) and 20 μl of 0.2M $CaCl_2$. The R-value (time to initial fibrin formation) was obtained for each sample and plotted versus relative concentration (set the lowest concentration as 1 for each (similar R-value), then increase subsequent concentrations 2×).

Figure 11:
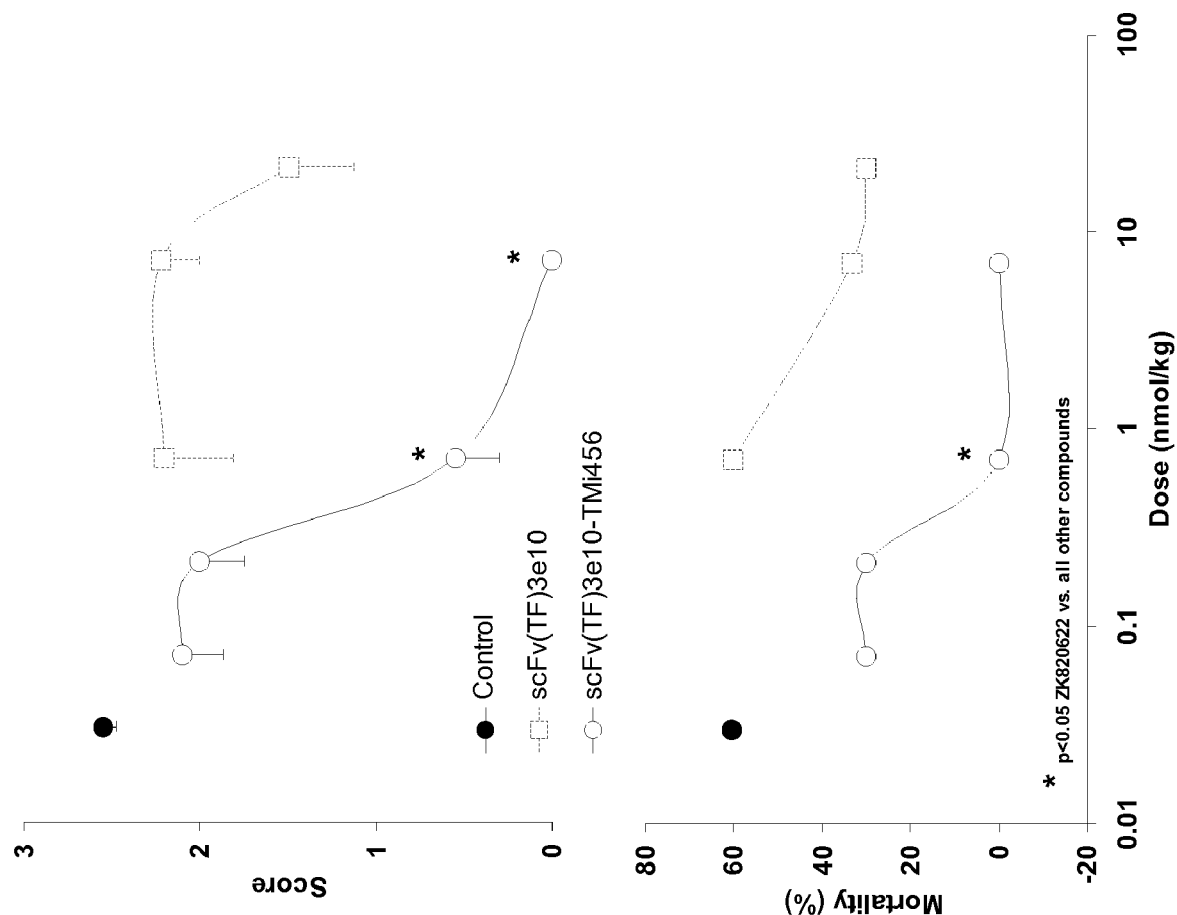

FIG. 11. The fusion protein scFV(TF)3e10-TMi456 is efficacious in an in vivo model of disseminated intravascular coagulation ("DIC"). TF antibody (scFV(TF)3e10) and fusion (scFV(TF)3e10-TMi456) were evaluated in the rat thromboembolism model described in Example 8 for (A) percent mortality and (B) morbidity-mortality score. (A) In the vehicle-treated group, the dose of TF used resulted in 60% lethality ($LD_{60}$). scFv(TF)3e10-TMi456 at 0.7 nmol/kg completely prevented death. In contrast, scFv(TF)3e10 at 0.7 nmol/kg had no impact on death. scFv(TF)3e10-TMi456 was more efficacious than a 10-fold higher dose of scFv(TF)3e10. (B) In the vehicle-treated group, the in vivo dose of TF resulted in an average morbidity-mortality score of 2.6, based on the following scoring system: 0=unaffected; 1=mild respiratory distress (recover within 30 min); 2=severe respiratory distress (moribund, recovery required more than 60 min); and 3=death. scFv(TF)3e10-TMi456 dose-dependently prevented TF induced death and respiratory distress with an $ED_{50}$ value of 0.46 nmol/kg (0.019 mg/kg). scFv(TF)3e10-TMi456 at 7.0 nmol/kg completely prevented both death and respiratory distress, and at 0.7 nmol/kg completely prevented death and significantly reduced respiratory distress. In contrast, scFv(TF)3e10 at 0.7 nmol/kg had no impact on death and little or no effect on respiratory distress. scFv(TF)3e10-TMi456 was more efficacious than a 10-fold higher dose of scFv(TF)3e10.

DETAILED DESCRIPTION OF THE INVENTION

The anticoagulant fusion protein of the present invention is comprised of a targeting protein that interacts with either tissue factor ("TF") or the factor VIIa/tissue factor ("FVIIa/TF") complex, which is operably linked to the thrombomodulin ("TM") EGF456 domain alone or in combination with at least one other TM domain selected from the group consisting of the N-terminal hydrophobic region domain, the EGF123 domain, the interdomain loop between EGF3 and EGF4, and the O-glycosylated Ser/Thr-rich domain, or analogs, fragments, derivatives or variants thereof.

DEFINITIONS

In describing the present invention, the following terms are defined as indicated below.

"Recombinant proteins or polypeptides" refer to proteins or polypeptides produced by recombinant DNA techniques, i.e., produced from cells, microbial or mammalian, transformed by an exogenous DNA construct encoding the desired polypeptide. Proteins or polypeptides expressed in most bacterial cultures will be free of glycan. Proteins or polypeptides expressed in yeast may have a glycosylation pattern different from that expressed in mammalian cells.

"Native" proteins or polypeptides refer to proteins or polypeptides recovered from a source occurring in nature. The term "native TM" would include naturally occurring TM and fragments thereof.

A DNA "coding sequence" is a DNA sequence which is transcribed into mRNA and translated into a polypeptide in a host cell when placed under the control of appropriate regulatory sequences. The boundaries of the coding sequence are determined by a start codon at the 5' N-terminus and a translation stop codon at the 3' C-terminus. A coding sequence can include prokaryotic sequences, cDNA from eukaryotic mRNA, genomic DNA sequences from eukaryotic DNA, and synthetic DNA sequences. A transcription termination sequence will usually be located 3' to the coding sequence.

"Fusion protein" is a protein resulting from the expression of at least two operatively linked heterologous coding sequences. The fusion protein of this invention is comprised of a targeting protein that interacts with either TF or the FVIIa/TF complex, which is operably linked to the thrombomodulin ("TM") EGF456 domain alone or in combination with at least one other TM domain selected from the group consisting of the N-terminal hydrophobic region domain, the EGF123 domain, the interdomain loop between EGF3 and EGF4, and the O-glycosylated Ser/Thr-rich domain, or analogs, fragments, derivatives or variants thereof.

"Targeting protein" is a protein that binds to or interacts with another protein or a protein complex. The targeting protein of this invention is a protein that binds to or interacts with TF or the FVIIa/TF complex. For example, an anti-TF or anti-FVIIa/TF complex antibody, is a targeting protein of this invention. Two other examples of targeting proteins are active site inhibited factor VIIa ("FVIIai"), which can bind TF to form an inactive FVIIai/TF complex, and tissue factor pathway inhibitor ("TFPI"), which can bind to and inactivate the FVIIa/TF complex.

"Nucleotide sequence" is a heteropolymer of deoxyribonucleotides (bases adenine, guanine, thymine, or cytosine). DNA sequences encoding the fusion proteins of this invention can be assembled from synthetic cDNA-derived DNA fragments and short oligonucleotide linkers to provide a synthetic gene that is capable of being expressed in a recombinant expression vector. In discussing the structure of particular double-stranded DNA molecules, sequences may be described herein according to the normal convention of giving only the sequence in the 5' to 3' direction along the nontranscribed strand of cDNA.

"Recombinant expression vector" is a replicable DNA construct used either to amplify or to express DNA encoding the fusion proteins of the present invention. An expression vector contains DNA control sequences and a coding sequence. DNA control sequences include promoter sequences, ribosome binding sites, polyadenylation signals, transcription termination sequences, upstream regulatory domains and enhancers. Recombinant expression systems as defined herein will express the fusion proteins upon induction of the regulatory elements.

"Transformed host cells" refer to cells that have been transformed and transfected with exogenous DNA. Exogenous DNA may or may not be integrated (covalently linked) to chromosomal DNA making up the genome of the cell. In prokaryotes and yeast, for example, the exogenous DNA may be maintained on an episomal element, such as a plasmid or stably integrated into chromosomal DNA. With respect to eukaryotic cells, a stably transformed cell is one in which the exogenous DNA has become integrated into the chromosome replication. This stability is demonstrated by the ability of the eukaryotic cell lines or clones to produce a population of daughter cells containing the exogenous DNA "Thrombomodulin (TM)" refers to an endothelial cell surface glycoprotein that forms a high affinity complex with thrombin. The genes encoding native TM (both its genomic form and as cDNA) have been isolated and sequenced from bovine and human (Jackman, R. W. et al. (1986) *Proc. Natl. Acad. Sci. USA* 83(23):8834-8838 and Jackman, R. W. et al. (1987) *Proc. Natl. Acad. Sci. USA* 84(18):6425-6429, both of which are herein incorporated by reference). The sequences for bovine, human and mouse TM exhibit a high degree of homology with one another. The cDNA of human TM encodes a 60.3 kDa protein of 575 amino acids, including a signal sequence of about 18 amino acids, see e.g., U.S. Pat. No. 5,827,824.

When thrombin binds to TM there may be one thousand-fold or more increase in the activation rate of protein C which forms the anticoagulant enzyme activated protein C. In addition, when thrombin is bound to TM, thrombin no longer works as a procoagulant enzyme. Specifically, thrombin-catalyzed fibrin formation, factor V activation, and platelet activation, are all inhibited in the presence of TM. Thus, TM converts thrombin into a physiological anticoagulant.

"Thrombomodulin (TM) domain" refers to a discrete amino acid sequence that can be associated with a particular function or characteristic of TM, such as a characteristic tertiary structural unit. The full-length TM gene (SEQ ID NO: 4) encodes a precursor or pro-polypeptide containing the following domains: amino acids −18−−1 is the signal sequence; amino acids 1-226 is the N-terminal hydrophobic region; amino acids 227-462 is the cysteine-rich region; consisting of 6 tandem EGF-like repeats joined by small interdomain peptides or loops; amino acids 463-497 is an O-glycosylated Ser/Thr-rich region; amino acids 498-521 is a hydrophobic transmembrane region; and amino acids 522-557 is the C-terminal cytoplasmic tail. The cysteine-rich region can be further divided into 3 domains: amino acids 226-344 is EGF123, consisting of the EGF-like repeats 1, 2 and 3 (residues 226-344); amino acids 345-349 is the interdomain loop between EGF3 and EGF4; and amino acids 350-462 is EGF456, consisting of the EGF-like domains 4, 5 and 6. See e.g., Yost, C. S. et al. (1983) *Cell* 34(3):759-766; Wen, D. Z. et al. (1987) *Biochemistry* 26(14):4350-4357; and Wang, W. et al. (2000), supra, all of which are incorporated herein by reference. The amino acid sequence of native thrombomodulin is given in SEQ ID NO: 5.

The terms "analog", "fragment", "derivative", and "variant", when referring to the fusion proteins of this invention, as well as the targeting proteins and the TM domain(s), means analogs, fragments, derivatives, and variants of the fusion proteins, targeting proteins and TM domain(s) which retain substantially the same biological function or activity, as described further below.

An "analog" includes a pro-polypeptide which includes within it, the amino acid sequence of the fusion protein of this invention. The active fusion protein of this invention can be cleaved from the additional amino acids that complete the pro-fusion protein molecule by natural, in vivo processes or by procedures well known in the art such as by enzymatic or chemical cleavage. For example, native TM is naturally expressed as a 575 amino acid pro-polypeptide which is then processed in vivo to release the 557 amino acid active mature polypeptide.

A "fragment" is a portion of the fusion protein, targeting protein or TM domain(s) which retains substantially similar functional activity, as shown in the in vitro assays disclosed herein as described further below.

A "derivative" includes all modifications to the fusion protein which substantially preserve the functions disclosed herein and include additional structure and attendant function, e.g., PEGylated fusion proteins which have greater half-life, O-glycosylated fusion proteins modified by the addition of chondroitin sulfate, and biotinylated fusion proteins, as described further below.

"Substantially similar functional activity" and "substantially the same biological function or activity" each means that the degree of biological activity that is within about 30% to 100% or more of that biological activity demonstrated by the polypeptide to which it is being compared when the biological activity of each polypeptide is determined by the same procedure or assay. For example, a fusion protein or TM domain(s) that has substantially similar functional activity to the fusion protein of Example 2 (SEQ ID NO:2) is one that, when tested in the protein C activation assay (chromogenic) described in Example 5, demonstrates accumulation of activated protein C. A targeting protein that has substantially similar functional activity to the anti-TF antibody of Example 1 (SEQ ID NO:1) is one that, when tested in the sTF/FVIIa assay or FX activation assays described in Example 5, demonstrates the ability to bind to or neutralize TF or the FVIIa/TF complex.

"Similarity" between two polypeptides is determined by comparing the amino acid sequence and its conserved amino acid substitutes of one polypeptide to the sequence of a second polypeptide. Such conservative substitutions include those described above in *The Atlas of Protein Sequence and Structure* 5 by Dayhoff (1978) and by Argos (1989) *EMBO J.*

8:779-785. For example, amino acids belonging to one of the following groups represent conservative changes:

Ala, Pro, Gly, Gln, Asn, Ser, Thr:

Cys, Ser, Tyr, Thr;

Val, lie, Leu, Met, Ala, Phe;

Lys, Arg, His;

Phe, Tyr, Trp, His; and

Asp, Glu.

All other technical terms used herein have the same meaning as is commonly used by those skilled in the art to which the present invention belongs.

Targeting Protein:

The targeting protein of this invention is a protein that has the ability to specifically bind to a particular preselected target molecule, e.g., TF or the FVIIa/TF complex, and then serves to direct the fusion protein to a cell or tissue bearing the preselected target molecule.

In one embodiment of this invention, the targeting protein is an antibody that can bind to and neutralize TF or the FVIIa/TF complex. "Antibody" as used herein includes intact immunoglobulin ("Ig") molecules, as well as fragments thereof, such as Fab, F(ab')$_2$, and Fv, which are capable of binding an epitope of TF or the FVIIa/TF complex. Typically, at least 6, 8, 10, or 12 contiguous amino acids are required to form an epitope. However, epitopes which involve non-contiguous amino acids may required more, e.g. at least 15, 25, or 50 amino acids.

Typically, an antibody that binds specifically to TF or the FVIIa/TF complex provides a detection signal at least 5-, 10-, or 20-fold higher than a detection signal provided with other proteins when used in an immunochemical assay. Preferably, antibodies that bind specifically to TF or the FVIIa/TF complex do not detect other proteins in immunochemical assays and can immunoprecipitate TF or the FVIIa/TF complex from solution.

TF or the FVIIa/TF complex can be used to immunize a mammal, such as a mouse, rat, rabbit, guinea pig, monkey, or human to produce polyclonal antibodies. If desired, TF or the FVIIa/TF complex can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g., lysolecithin, pluronic polyols, polyanions, peptides, oil emulsions, keyhole limpet hemocyanin, and dinitrophenol). Among adjuvants used in humans, BCG (bacilli Calmette-Guerin) and *Cornybacterium parvum* are especially useful.

Monoclonal antibodies that bind specifically to TF or the FVIIa/TF complex can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al. (1985) *Nature* 256:495-497; Kozbor et al. (1985) *J. Immunol. Methods* 81:31-42; Cote et al. (1983) *Proc. Natl. Acad. Sci. USA* 80:2026-2030; and Cote et al. (1984) *Mol. Cell Biol.* 62:109-120).

In addition, techniques developed for the production of "chimeric antibodies," the splicing of mouse antibody genes to human antibody genes to obtain a molecule with appropriate antigen specificity and biological activity, can be used (Morrison et al. (1984) *Proc. Natl. Acad. Sci. USA* 81:6851-6855; Neuberger et al. (1984) *Nature* 312:604-608; Takeda et al. (1985) *Nature* 314:452-454). Monoclonal and other antibodies also can be "humanized" to prevent a patient from mounting an immune response against the antibody when it is used therapeutically. Such antibodies may be sufficiently similar in sequence to human antibodies to be used directly in the fusion protein or may require alteration of a few key residues. Sequence differences between rodent antibodies and human sequences can be minimized by replacing residues which differ from those in the human sequences by site directed mutagenesis of individual residues or by grafting of entire complementarity determining regions. Alternatively, humanized antibodies can be produced using recombinant methods, as described in GB2188638B. Antibodies that bind specifically to TF or the FVIIa/TF complex can contain antigen-binding sites which are either partially or fully humanized, as disclosed in U.S. Pat. No. 5,565,332.

Alternatively, techniques described for the production of single chain antibodies can be adapted using methods known in the art to produce single chain antibodies that specifically bind to TF or the FVIIa/TF complex. Antibodies with related specificity, but of distinct idiotypic composition, can be generated by chain shuffling from random combinatorial Ig libraries (Burton (1991) *Proc. Natl. Acad. Sci. USA* 88:11120-11123).

Single chain antibodies also can be constructed using a DNA amplification method, such as PCR, using hybridoma cDNA as a template (Thirion et al. (1996) *Eur. J. Cancer Prev.* 5:507-511). Single chain antibodies can be mono- or bispecific, and can be bivalent or tetravalent. Construction of tetravalent, bispecific single chain antibodies is taught, for example, in Coloma and Morrison (1997) *Natl. Biotechnol.* 15:159-163. Construction of bivalent, bispecific single chain antibodies is taught in Mallendar and Voss (1994) *J. Biol. Chem.* 269:199-216.

A nucleotide sequence encoding a single chain antibody can be constructed using manual or automated nucleotide synthesis, cloned into an expression construct using standard recombinant DNA methods, and introduced into a cell to express the coding sequence. Alternatively, single chain antibodies can be produced directly using, for example, filamentous phage display technology (Verhaar et al. (1995) *Int. J. Cancer* 61:497-501; and Nicholls et al. (1993) *J. Immunol. Meth.* 165:81-91).

Antibodies that bind specifically to TF or the FVIIa/TF complex can also be produced by inducing in vivo production in the lymphocyte population or by screening Ig libraries or panels of highly specific binding reagents as disclosed in the literature. (Orlandi et al. (1989) *Proc. Natl. Acad. Sci. USA* 86:3833-3837; Winter et al. (1991) *Nature* 349:293-299).

In another embodiment of this invention, the targeting protein is a targeting moiety other than an antibody that can bind to and neutralize TF. Two such examples are active site inhibited factor FVIIa (FVIIai) and tissue factor pathway inhibitor (TFPI).

Both FVIIa and FVIIai form a high affinity complex with TF (Sorenson, B. B. and Rao, L. V. (1998) *Blood Coagul. Fibrinolysis* 9(Suppl 1):S67-71). FVIIai is a TF neutralizing anticoagulant that acts by competing with endogenous FVIIa for binding to exposed TF. FVIIai inhibits the ability of proteolytically active FVIIa to form a competent FVIIa-TF complex and in this way inhibits initiation of coagulation. By genetically fusing TM domains to FVIIai, TM could be targeted to TF-rich prothrombotic surfaces.

The cDNA encoding human FVII has been isolated and sequenced (Hagen, H. S. et al. (1986) *Proc. Natl. Acad. Sci.*

USA 83(8):2412-2416, which is incorporated herein by reference). The human FVII cDNA can be made by standard recombinant DNA techniques starting from mRNA isolated from human liver. FVIIai can be made by mutating the active site serine by standard recombinant DNA techniques or by chemically treating catalytically active FVIIa with a peptidyl chloromethylketone, which irreversibly modifies and inhibits the active site.

TFPI targets and inhibits the FVIIa/TF complex in a FXa dependent fashion (Salemink, I. et al. (1999) *J. Biol. Chem.* 274(40):28225-28232). TFPI first binds to FXa and then the TFPI-FXa complex binds to and inhibits the FVIIa/TF complex. By genetically fusing TM domains to TFPI, TM could be targeted to TF-rich prothrombotic surfaces.

The cDNA encoding human TFPI has been isolated and sequenced (Wun, T. C. et al. (1988) *J. Biol. Chem.* 263(13): 6001-6004, which is incorporated herein by reference). The human TFPI cDNA can be made by standard recombinant DNA techniques starting from mRNA isolated from human liver.

The targeting protein of this invention (i.e, antibodies or other relevant proteins) can be expressed and purified by methods well known in the art. For example, antibodies and proteins can be affinity purified by passage over a column to which TF is bound. The bound antibodies or proteins can then be eluted from the column using a buffer with a high salt concentration.

In one preferred embodiment of this invention, the targeting protein is a TF-binding scFv antibody that inhibits activation of FX by the FVIIa/TF complex and does not compete with FVIIa binding. In order to produce the TF-binding scFv antibody, the human antibody library HuPhaBL3, which was displayed on filamentous phage, was selected against immobilized soluble TF. Antibodies from TF binding phage were overexpressed in *E. coli* and affinity purified using an e-tag column. The purified antibodies were further characterized using BIAcore, a sTF dependent factor VIIa assay (sTF/FVIIa assay), a FX activation assay, and the PT assay. The sequence of the TF-binding scFv antibody, designated scFv(TF)3e10, is shown in Example 1 and corresponds to SEQ ID NO:1. The isolation, production and characterization of the TF-binding scFV antibody are described in greater detail below.

Thrombomodulin:

The TM domain(s) portion of the fusion protein acts as a cofactor for thrombin catalyzed activation of protein C, which in turn degrades factors Va and VIIIa thereby preventing further thrombus formation. The domains of TM include e.g., the N-terminal hydrophobic region domain, the EGF123 domain, the interdomain loop between EGF3 and EGF4, the EGF456 domain, and the O-glycosylated Ser/Thr-rich region domain. The EGF456 domain, in particular, mediates thrombin binding and protein C activation (Kurosawa, S. et al. (1988), supra; and Zushi, M. et al. (1989) supra). In preferred embodiments of this invention, the TM domain(s) portion of the fusion protein comprises the EGF456 domain alone or in combination with one or more of the other TM domains. In still more preferred embodiments of this invention, the EGF456 domain contains point mutations that render the protein more resistant to oxidative damage and proteases and/or increase its catalytic efficiency.

The full length DNA sequence encoding human TM facilitates the preparation of genes and is used as a starting point to construct DNA sequences encoding TM peptides and fusion proteins containing TM and fragments/peptides of TM.

The full-length gene for TM can be prepared by several methods. Human genomic libraries are commercially available. Oligonucleotide probes, specific to these genes, can be synthesized using the published gene sequence. Methods for screening genomic libraries with oligonucleotide probes are known. The publication of the gene sequence for TM demonstrates that there are no introns within the coding region. Thus, a genomic clone provides the necessary starting material to construct an expression plasmid for TM using known methods.

A TM encoding DNA fragment can be retrieved by taking advantage of restriction endonuclease sites that have been identified in regions which flank or are internal to the gene. (Jackman, R. W. et al. (1987), supra). Alternately, the full-length genes can also be obtained from a cDNA bank. For example, messenger RNA prepared from endothelial cells provides suitable starting material from the preparation of cDNA. Methods for making cDNA banks are well known (see e.g., Sambrook, J. F. et al., *Molecular Cloning: A Laboratory Manual*, Cold Spring Harbor Laboratory (1989), which is herein incorporated by reference).

Fusion Protein:

The anticoagulant fusion protein of this invention comprises a targeting protein that binds to either TF or the FVIIa/ TF complex, and which is operably linked to the TM EGF456 domain alone or in combination with at least one other TM domain selected from the group consisting of the N-terminal hydrophobic region domain, the EGF123 domain, the interdomain loop between EGF3 and EGF4, and the O-glycosylated Ser/Thr-rich domain, or analogs, fragments, derivatives or variants thereof. The fusion protein can comprise the targeting protein linked with the domains of TM in any combination.

In one particularly preferred embodiment, the fusion protein comprises an antibody that binds TF, operably linked to the TM EGF456 domain and the interdomain loop between EGF3 and EGF4 ("TMi456"), or analogs, fragments, derivatives or variants thereof.

The fusion protein of the present invention includes, but it not limited to, constructs in which the C-terminal portion of a single chain antibody is fused to the N-terminal portion of an analog, fragment, derivative or variant of a TM domain(s), the C-terminal portion of an IgG antibody is fused to the N-terminal portion of an analog, fragment, derivative or variant of a TM domain(s), the C-terminal portion of an Fab antibody is fused to the N-terminal portion of an analog, fragment, derivative or variant of a TM domain(s), the N-terminal portion of a single chain antibody is fused to the C-terminal portion of an analog, fragment, derivative or variant of a TM domain(s), the N-terminal portion of an IgG antibody is fused to the C-terminal portion of an analog, fragment, derivative or variant of a TM domain(s), the N-terminal portion of an Fab antibody is fused to the C-terminal portion of an analog, fragment, derivative or variant of a TM domain(s), more than one single chain antibody is fused to both the N-terminal and the C-terminal portions of an analog, fragment, derivative or variant of a TM domain(s), more than one IgG antibody is fused to both the N-terminal and the C-terminal portions of an analog, fragment, derivative or variant of a TM domain(s), more than one Fab antibody is fused to both the N-terminal and the C-terminal portions of an analog, fragment, derivative or variant of a TM domain(s), more than one analog, fragment, derivative or variant of a TM domain(s) is fused to both the N-terminal and the C-terminal portions of a single chain antibody, more than one analog, fragment, derivative or variant of a TM domain(s) is fused to both the N-terminal and the C-terminal portions of an IgG antibody, more than one analog, fragment, derivative or variant of a TM domain(s) is fused to both the N-terminal and the C-terminal portions of an Fab antibody, one or more than one analog, fragment, derivative or variant of a TM domain(s) is fused to both the N-terminal and the C-terminal portions of a dimeric single chain antibody.

The fusion proteins of the present invention include the fusion proteins of Examples 2 (SEQ ID NO:2) and 3 (SEQ ID NO: 3), as well as those fusion proteins having insubstantial variations in sequence from them. An "insubstantial variation" would include any sequence, substitution, or deletion variant that maintains substantially at least one biological function of the polypeptides of this invention, preferably cofactor activity for thrombin-mediated protein C activation. These functional equivalents may preferably include fusion proteins which have at least about a 90% identity to the fusion proteins of SEQ ID NOs:2 or 3, and more preferably at least a 95% identity to the fusion proteins of SEQ ID NOs:2 or 3, and still more preferably at least a 97% identity to the fusion proteins of SEQ ID NOs:2 or 3, and also include portions of such fusion proteins having substantially the same biological activity. However, any fusion protein having insubstantial variation in amino acid sequence from the fusion proteins of SEQ ID NOs:2 and 3 that demonstrates functional equivalency as described further herein is included in the description of the present invention.

In another embodiment, the fusion protein comprises an antibody that binds TF operably linked to TM domain EGF3, which is required to activate thrombin-activatable fibrinolysis activator (TAFI).

Analogs, Fragments, Derivatives and Variants:

An analog, fragment, derivative, or variant of the fusion proteins, as well as targeting proteins or TM domain(s), of the present invention may be: (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues includes a substituent group, or (iii) one in which the mature fusion protein is fused with another compound, such as a compound to increase the half-life of the fusion protein (for example, polyethylene glycol), or (iv) one in which additional amino acids are fused to the mature fusion protein, such as a leader or secretory sequence or a sequence which is employed for purification of the mature fusion protein, or (v) one in which the polypeptide sequence is fused with a larger polypeptide, i.e., human albumin, an antibody or Fc, for increased duration of effect. Such analogs, fragments, derivatives, and variants are deemed to be within the scope of those skilled in the art from the teachings herein.

Preferably, the derivatives of the present invention will contain conservative amino acid substitutions (defined further below) made at one or more predicted, preferably non-essential amino acid residues. A "nonessential" amino acid residue is a residue that can be altered from the wild-type sequence of a protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Non-conservative substitutions would not be made for conserved amino acid residues or for amino acid residues residing within a conserved protein domain, unless the non-conservative substitutions are made to render the resulting fusion protein more resistant to oxidative damage and proteases and/or increase its catalytic efficiency. Fragments or biologically active portions include polypeptide fragments suitable for use as a medicament, as a research reagent, and the like. Fragments include peptides comprising amino acid sequences sufficiently similar to or derived from the amino acid sequences of a fusion protein of this invention and exhibiting at least one activity of that polypeptide, but which include fewer amino acids than the full-length polypeptides disclosed herein. Typically, biologically active portions comprise a domain or motif with at least one activity of the polypeptide. A biologically active portion of a polypeptide can be a peptide that is, for example, 5 or more amino acids in length. Such biologically active portions can be prepared synthetically or by recombinant techniques and can be evaluated for one or more of the functional activities of a polypeptide of this invention by means disclosed herein and/or well known in the art.

Moreover, preferred derivatives of the present invention include mature fusion proteins that have been fused with another compound, such as a compound to increase the half-life of the polypeptide and/or to reduce potential immunogenicity of the polypeptide (for example, polyethylene glycol, "PEG"). The PEG can be used to impart water solubility, size, slow rate of kidney clearance, and reduced immunogenicity to the fusion protein. See e.g., U.S. Pat. No. 6,214,966. In the case of PEGylations, the fusion of the fusion protein to PEG can be accomplished by any means known to one skilled in the art. For example, PEGylation can be accomplished by first introducing a cysteine mutation into the fusion protein, followed by site-specific derivatization with PEG-maleimide. The cysteine can be added to the C-terminus of the peptides. See, e.g., Tsutsumi et al. (2000) Proc. Natl. Acad. Sci. USA 97(15):8548-8553. Another modification which can be made to the fusion protein involves biotinylation. In certain instances, it may be useful to have the fusion protein biotinylated so that it can readily react with streptavidin. Methods for biotinylation of proteins are well known in the art. Additionally, chondroitin sulfate can be linked with the fusion protein.

Variants of the fusion proteins, targeting proteins and TM domain(s) of this invention include polypeptides having an amino acid sequence sufficiently similar to the amino acid sequence of the original fusion proteins, targeting proteins and TM domain(s). The term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that contain a common structural domain that is at least about 45%, preferably about 75% through 98%, identical are defined herein as sufficiently similar. Preferably, variants will be sufficiently similar to the amino acid sequence of the preferred fusion proteins of this invention. Variants include variants of fusion proteins encoded by a polynucleotide that hybridizes to a polynucleotide of this invention or a complement thereof under stringent conditions. Such variants generally retain the functional activity of the fusion proteins of this invention. Libraries of fragments of the polynucleotides can be used to generate a variegated population of fragments for screening and subsequent selection. For example, a library of fragments can be generated by treating a double-stranded PCR fragment of a polynucleotide with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the fusion proteins of this invention.

Variants include fusion proteins, as well as targeting proteins and TM domain(s), that differ in amino acid sequence due to mutagenesis. Variants that have cofactor activity for thrombin-mediated protein C activation can be identified by screening combinatorial libraries of mutants, for example truncation or point mutants, of the fusion proteins or TM domain(s) of this invention using the protein C activation assay described in Example 5. Variants that have TF- or FVIIa/TF complex-binding activity can be identified by screening combinatorial libraries of mutants, for example truncation or point mutants, of the fusion proteins or targeting proteins of this invention using the sTF/FVIIa assay or FX activation assays of Example 5 described in Example 5. In addition, bioequivalent analogs of the fusion proteins may also be constructed by making various substitutions on residues or sequences in the TM domain(s) portion of the fusion protein which can render the fusion protein more oxidation damage or protease resistant, see e.g., U.S. Pat. No. 5,827,824, or increase the catalytic efficiency of the fusion protein, see e.g., Adler, M. et al. (1995) *J. Biol. Chem.* 270(40):23366-23372, and PCT patent application WO01/98352, published 27 Dec. 2001, all of which are fully incorporated herein by reference.

In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential variant amino acid sequences is expressible as individual polypeptides, or, alternately, as a set of larger fusion proteins (for example, for phage display) containing the set of sequences therein. There are a variety of methods that can be used to produce libraries of potential variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential variant sequences. Methods for synthesizing degenerate oligonucleotides are known in the art (see, e.g., Narang (1983) *Tetrahedron* 39:3; Itakura et al. (1984a) *Annu. Rev. Biochem.* 53:323; Itakura et al. (1984b) *Science* 198:1056; Ike et al. (1983) *Nucleic Acid Res.* 11:477).

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of fusion proteins, as well as targeting proteins and TM domain(s), for cofactor activity for thrombin-mediated protein C activation or TF- or FVIIa/TF complex-binding activity. The most widely used techniques, which are amenable to high throughput analysis for screening large gene libraries typically include cloning the gene library into replicable expression vectors, transforming appropriate cells with the resulting library of vectors and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify the desired variants.

Producing Fusion Proteins:

The fusion protein of this invention is produced by fusing the targeting protein to, or otherwise binding it to, the TM domain(s) or analogs, fragments, derivatives or variants thereof by any method known to those skilled in the art. The two components may be chemically bonded together by any of a variety of well-known chemical procedures. For example, the linkage may be by way of heterobifunctional cross-linkers, e.g., SPDP, carbodiimide, glutaraldehyde, or the like.

In a more preferred embodiment, the targeting protein of this invention can be fused to the TM domain(s) by recombinant means such as through the use of recombinant DNA techniques to produce a nucleic acid which encodes both the targeting protein and the polypeptide encoding the TM domain(s) and expressing the DNA sequence in a host cell such as *E. coli* or a mammalian cell. The DNA encoding the fusion protein may be cloned in cDNA or in genomic form by any cloning procedure known to those skilled in the art. See for example, Sambrook, J. F. et al. (1989) supra.

In the case where the targeting protein is an antibody, once a DNA sequence has been identified that encodes a Fv region which when expressed shows specific binding activity, fusion proteins comprising that Fv region may be prepared by methods known to one of skill in the art. Thus, for example, Chaudhary, V. K. et al. (1989) *Nature* 339(6223): 394-397; Batra, J. K. et al. (1990) *J. Biol. Chem.* 265(25):15198-15202; Batra, J. K. et al. (1989) *Proc. Natl. Acad. Sci. USA* 86(21): 8545-8549; Chaudhary, V. K. et al. (1990) *Proc. Natl. Acad. Sci. USA* 87(3):1066-1070, all incorporated by reference, describe the preparation of various single chain antibody fusion proteins. The Fv region may be fused directly to the TM domain(s) or may be joined via a linker sequence. The linker sequence may be present simply to provide space between the targeting moiety and the TM domain(s) or to facilitate mobility between these regions to enable them to each attain their optimum conformation. The DNA sequence comprising the connector may also provide sequences (such as primer or restriction sites) to facilitate cloning or may preserve the reading frame between the sequence encoding the targeting moiety and the sequence encoding the TM domain(s). The design of such connector peptides will be well known to those of skill in the art.

In the present invention, linker sequences can be used for linking the targeting protein with the TM domain(s). In one preferred embodiment of the present invention, two linker sequences are used in constructing a fusion protein comprised of a single chain antibody and the TM EGF456 domain and the interdomain loop between EGF3 and EGF4 (TMi456). The first links the heavy and light domains of the single chain antibody. The first linker sequence is 5 amino acids in length. It will be apparent that other short linker sequences, from 0 to 10 amino acids may be used. The second linker in the present invention is a 15 amino acid linker that links the antibody to the TM domain(s). It will be apparent to those of skill in the art that many different linker sequences may be used and still result in a fusion protein which retains anticoagulant activity and the activation of protein C. Modifications of the existing linker will be aimed at maximizing the enhancement of protein C activation on TF-containing phospholipid surfaces.

In a preferred approach, the single chain antibody was prepared using a phage display library. In the first step of constructing a phage display library, the variable genes ($V_H$ (from IgM) $V_K$ and $V_L$) were PCR cloned from pooled mRNA from human bone marrow, lymph node and spleen using a set of family specific primers. The resultant pCITE-$V_H$ ($3.8\times10^9$ members), pZ604-$V_K$ ($1.6\times10^7$) and pZ604-$V_L$ ($3.2\times10^7$) libraries represent a permanent and high diversity of V genes. The $V_H$ genes were amplified from PCITE-$V_H$ library. The $V_K$ and $V_L$ genes were PCR amplified from the pZ604-$V_K$ and pZ604-$V_L$ library with reverse $J_H$ and linker sequence at the 5'end. The gel purified $V_H$, $V_K$, and $V_L$ containing PCR products were then spliced together to make the scFv gene repertoire. The scFV gene repertoire was cloned to a phagemid vector pZ603, and the ligation product was electroporated into competent TG1 *E. coli* cells to generate the scFV phage display library, HuPhabL3, with $5.2\times10^9$ individual transformants (Kay, B. K. et al. (1996) *Phage Display of Peptides and Proteins: A Laboratory Manual*, Academic Press, San Diego Calif.; Marks, J. D. et al. (1991) *J. Mol. Biol.* 222(3):581-597; Sheets, M. D. et al. (1998) *Proc. Natl. Acad. Sci. USA* 95(11): 6157-6162).

In a preferred embodiment of the present invention, a single chain antibody (scFv(TF)3e10) was prepared which has a single $V_H/V_L$ binding site for TF. The amino acid sequence of scFv(TF)3e10 (SEQ ID NO:1), is depicted in Example 1.

In a preferred embodiment of the present invention, a PCR fragment containing the TMi456 sequence (with M388L and H381G mutations) flanked by Notl sites was subcloned into the Notl site of pZ612/3e10 (a bacterial expression vector for scFv(TF)3e10 based on pCANTAB5 from Pharmacia). Herein, point mutations in the TM portions of the fusion proteins of the invention are specified the single letter designation of the amino acid residue of native TM, followed by the amino acid position number in mature TM and the single letter designation of the amino acid mutation. For example, M388L indicates that the methionine at amino acid position 388 of mature TM has been changed to leucine. The Notl site is between the antibody sequence and the e-tag sequence. This generated a bacterial expression construct (pKM101) for a fusion protein comprised of the scFV(TF)3e10—a 15 amino acid linker—TMi456, followed by the e-tag sequence. To generate a mammalian expression vector a PCR fragment was first generated from the pKM101 template. This fragment was designed for ligation into the Stul/Mscl sites of the TM expression vector pTHR525. This generated a vector (pKM113) that had the Solulin signal sequence followed by the sequence for the mature fusion protein followed by the e-tag sequence. The vector contains the ampicillin resistance gene and the hydromycin and DHFR selection markers. The expression is driven by the MPSV LTR promoter. Site directed mutagenesis was performed on this vector to include the R456G and H457Q mutations which confer protease resistance to the TM portion. The resulting vector is referred to as pKM115. The pMK115 vector had a 15 amino acid linker separating the $V_H$ and $V_L$ domains and another 15 amino acid linker separating the $V_L$ domain from the TMi456. The linker separating the $V_H$ and $V_L$ was decreased to 5 amino acids to drive the formation of a higher avidity dimer, referred to as pHM115.5. The fusion protein encoded by pHM115.5, scFv(TF)3e10-TMi456 (SEQ ID NO: 2), is depicted in Example 2. An additional vector, pKM125, was generated using standard recombinant DNA technology by deleting 3 amino acids (GAP) between the 5 amino acid linker separating the $V_H$ and $V_L$ domains and deleting the e-tag at the C-terminus of the fusion protein. The resulting fusion protein, scFv(TF)3e10-TMi456Δ (SEQ ID NO:3), is depicted in Example 3.

Expression and Purification of Fusion Proteins:

There are several ways to express the recombinant fusion proteins in vitro, including *E. coli*, baculovirus, yeast mammalian cells or other expression systems. Methods for the expression of cloned genes in bacteria are well known. To obtain high level expression of a cloned gene in a prokaryotic system, it is essential to construct expression vectors which contain, at the minimum, a strong promoter to direct mRNA transcription termination. Examples of regulatory regions suitable for this purpose are the promoter and operator region of the *E. coli* beta-glucosidase gene, the *E. coli* tryptophan biosynthetic pathway, or the leftward promoter from phage Lambda. The inclusion of selection markers in DNA vectors transformed in *E. coli* is useful. Examples of such markers include the genes specifying resistance to ampicillin, tetracycline, or chloramphenicol.

Of the higher eukaryotic cell systems useful for expression of the fusion proteins and analogs, thereof, there are numerous cell systems to select from. Illustrative examples of mammalian cell lines include but are not limited to RPMI 7932, VERO and HeLa cells, Chinese hamster ovary (CHO) cell lines, WI38, BHK, COS-7, C127 or MDCK cell lines. A preferred mammalian cell lines is CHL-1. When CHL-1 is used hygromycin is included as a eukaryotic selection marker. CHL-1 cells are derived from RPMI 7032 melanoma cells, a readily available human cell line. The CHL-1 cell line has been deposited with ATCC according to conditions of the Budapest Treaty and has been assigned #CRL 9446, deposited Jun. 18, 1987. Cells suitable for use in this invention car commercially available from the ATCC. Illustrative cell lines include *Spodoptera frugiperda* and *Bombyx mori*.

The prokaryotic system, *E. coli*, is not able to do post-translational modification, such as glycosylation. In addition proteins with complex disulfide patterns are often misfolded when expressed in *E. coli*. For the fusion protein described herein there was a marked reduction in the thrombomodulin cofactor activity when expressed in *E. coli* although both activities were still present. With the prokaryotic system, the expressed protein is either present in the cell cytoplasm in an insoluble form so-called inclusion bodies, found in the soluble fraction after the cell has lysed, or is directed into the periplasm by addition of appropriate secretion signal sequences. If the expressed protein is in insoluble inclusion bodies, solubilization and subsequent refolding of the inclusion bodies is usually required.

Many prokaryotic expression vectors are known to those of skill in the art such as pKK223-3 (Pharmacia Fine Chemicals, Uppsala, Sweden), pKK233-2 (Clontech, Palo Alto, Calif., USA), and pGEM1 (Promega Biotech, Madison, Wis., USA), which are commercially available.

Promoters commonly used in recombinant microbial expression systems include the beta-lactamase (penicillinase) and lactose promoter system (Chang, A. C. et al. (1978) *Nature* 275(5681):617-624; Goeddel, D. V. et al. (1979) *Nature* 281(5732):544-548), the tryptophan (trp) promoter system (Goeddel, D. V. et al. (1980) *Nucl. Acids Res.* 8(18): 4057-4074) and tac promoter (Maniatis, T. et al., Molecular Cloning: A Laboratory Manual, Cold Spring Harbor Laboratory (1982)). Another useful bacterial expression system employs the lambda phage pL promoter and clts857 thermoinducible repressor (Bernard, H. U. et al. (1979) *Gene* 5(1):59-76; Love, C. A. et al. (1996) *Gene* 176(1-2):49-53). Recombinant fusion proteins may also be expressed in yeast hosts such as *Saccharomyces cerevisiae*. It usually gives the ability to do various post-translational modifications. The expressed fusion protein can be secreted into the culture supernatant where not many other proteins reside, making purification easier. Yeast vectors for expression of the fusion proteins in this invention contain certain requisite features. The elements of the vector are generally derived from yeast and bacteria to permit propagation of the plasmid in both. The bacterial elements include an origin of replication and a selectable marker. The yeast elements include an origin of replication sequence (ARS), a selectable marker, a promoter, and a transcriptional terminator.

Suitable promoters in yeast vectors for expression include the promoters of TRP1 gene, the ADH1 or ADHII gene, acid phosphatase (PH03 or PH05) gene, isocytochrome gene, or the promoters involved with the glycolytic pathway, such as the promoter of enolase, glyceraldehyde-3-phosphate dehydrogenase (GADPH), 3-phosphoglycerate kinase (PGK), hexokinase, pyruvate kinase, triosephosphate isomerase and phosphoglucose isomerase (Hitzeman, R. A. et al. (1980) *J. Biol. Chem.* 255(24):12073-12080; Hess, B. et al. (1968) *J. Adv. Enzyme Reg.* 7:149-167; and Holland, M. J. and Holland, J. P. (1978) *Biochemistry* 17(23):4900-4907).

Commercially available yeast vectors include pYES2, pPIC9 (Invitrogen, San Diego, Calif.), Yepc-pADH2a, pYcDE-1 (Washington Research, Seattle, Wash.), pBC102-K22 (ATCC #67255), and YpGX265GAL4 (ATCC #67233). Mammalian cell lines including but not limited to COS-7, L cells, C127, 3T3, Chinese Hamster Ovary (CHO), HeLa, BHK, CHL-1, NSO, and HEK293 can be employed to express the recombinant fusion proteins in this invention. The recombinant proteins produced in mammalian cells are normally soluble and glycosylated and have authentic N-termini. Mammalian expression vectors may contain non-transcribed elements such as an origin of replication, promoter and enhancer, and 5' or 3' nontranslated sequences such as ribosome binding sites, a polyadenylation site, acceptor site and splice donor, and transcriptional termination sequences. Promoters for use in mammalian expression vectors usually are for example viral promoters such as Polyoma, Adenovirus, HTLV, Simian Virus 40 (SV 40), and human cytomegalovirus (CMV).

Depending on the expression system and host selected, a homogeneous recombinant fusion protein can be obtained by using various combinations of conventional chromatography used for protein purification. These include: immunoaffinity chromatography, reverse phase chromatography, cation exchange chromatography, anion exchange chromatography, hydrophobic interaction chromatography, gel filtration chromatography, and HPLC If the expression system secretes the fusion protein into the growth media, the protein can be purified directly from the media. If the fusion protein is not secreted, it is isolated from cell lysates. Cell disruption can be done by any conventional method, including freeze-thaw cycling, sonication, mechanical disruption, or use of cell lysing agents.

In a preferred embodiment of this invention, the mammalian expression constructs were transfected into CHO DXB11 cells. Stable populations were selected using 400 μg/ml hygromycin B in HAMS/F12 medium. Expression levels were approximately 500 μg/L. To increase expression levels a population was selected using 100 nM methotrexate in alpha MEM medium. The approximate expression level of this population was 5 mg/L.

The fusion construct contains the e-tag sequence at the C-terminus of the protein. Anti-e-tag affinity columns were purchased from American/Pharmacia Biotech. Cell culture media was filtered through a 0.22 μm filter and loaded into 5 ml e-tag column at 2 ml/min. The column was washed with 0.2 M phosphate buffer 0.05% $NaN_3$, pH 7.0, and then collected into tubes containing 0.1 volume 1M Tris buffer, pH 8.2 to neutralize the elution buffer. Alternately, the filtered culture medium was loaded onto a protein A column. In this case, the column was washed with 50 mM citric acid, 300 mM NaCl, pH 6.5 and eluted with the same buffer at pH 3.0. In both cases, the purified samples were subsequently loaded onto a Sephadex 200 column to separate monomer from dimer forms of the fusion protein.

Pharmaceutical Compositions:

The invention also provides pharmaceutical compositions which can be administered to a patient to achieve a therapeutic effect. Pharmaceutical compositions of this invention can be prepared for administration by combining fusion protein having the desired degree of purity and the pharmaceutically effective amount with physiologically acceptable carriers.

The fusion proteins of the present invention can be used in pharmaceutical compositions, for intravenous administration or subcutaneous administration or intrathecal administration. Thus, the above described fusion proteins preferably will be combined with an acceptable sterile pharmaceutical carrier, such as five percent dextrose, lactated Ringer's solution, normal saline, sterile water, or any other commercially prepared physiological buffer solution designed for intravenous infusion. It will be understood that the selection of the carrier solution and the dosage and administration of the composition will vary with the subject and the particular clinical setting, and will be governed by standard medical procedures.

In accordance with the methods of the present invention, these pharmaceutical compositions may be administered in amounts effective to inhibit the pathological consequences associated with excess thrombin generation in the subject.

Administration of the fusion protein may be by a bolus intravenous injection, by a constant intravenous infusion or by a combination of both routes. Alternatively, or in addition, the fusion protein mixed with appropriate excipients may be taken into the circulation from an intramuscular site. Systemic treatment with fusion protein can be monitored by determining the activated partial thromboplastin time (PT) on serial samples of blood taken from patient. The coagulation time observed in this assay is prolonged when a sufficient level of the fusion protein is achieved in the circulation.

The recombinant fusion proteins and pharmaceutical compositions of this invention are useful for parenteral, topical, intravenous, oral or local administration. The pharmaceutical compositions can be administered in a variety of unit dosage forms depending upon the method of administration. For example, unit dosage forms can be administered in the form including but not limited to tablets, capsules, powder, solutions, and emulsions.

The recombinant fusion proteins and pharmaceutical compositions of this invention are particularly useful for intravenous administration. The compositions for administration will commonly comprise a solution of the single chain antibody or a fusion protein comprising the single chain antibody dissolved in a pharmaceutically acceptable carrier, preferably in an aqueous carrier. A variety of aqueous carriers can be used, e.g., buffered saline and the like. These solutions are sterile and generally free of undesirable matter. The compositions may be sterilized by conventional, well known sterilization techniques.

A typical pharmaceutical composition for intravenous administration can be readily determined by one of ordinary skill in the art. The amounts administered are clearly protein specific and depend on its potency and pharmacokinetic profile. Actual methods for preparing parenterally administrable compositions will be known or apparent to those skilled in the art and are described in more detail in such publications as Remington's Pharmaceutical Science, 15$^{th}$ ed., Mack Publishing Company, Easton, Pa. (1980).

The compositions containing the present fusion proteins or a cocktail thereof (i.e., with other proteins) can be administered as therapeutic treatments. In therapeutic applications, compositions are administered to a patient suffering from a bleeding disorder or disease in an amount sufficient to cure or at least partially arrest the bleeding. An amount adequate to accomplish this is defined as a "therapeutically effective amount". Amounts effective for this use will depend upon the severity of the disease and the general state of the patient's health.

Single or multiple administration of the compositions may be administered depending on the dosage and frequency as required and tolerated by the patient. In any event, the composition should provide a sufficient quantity of the proteins of this invention to effectively treat the patient.

The fusion proteins of the invention, or their pharmaceutically acceptable compositions, are administered in a therapeutically effective amount, which will vary depending upon a variety of factors including the activity of the specific fusion protein employed; the metabolic stability and length of action of the fusion protein; the age, body weight, general health, sex, and diet of the patient; the mode and time of administration; the rate of excretion; the drug combination; the severity of the particular disease-states; and the host undergoing therapy. Generally, a daily therapeutically effective amount is from about 0.14 mg to about 14.3 mg/kg of body weight per day of a fusion protein of the invention, or a pharmaceutically acceptable composition thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a fusion protein of the invention, or a pharmaceutically acceptable composition thereof, preferably from about 50 mg to about 700 mg per day, and most preferably from about 100 mg to about 500 mg per day.

Gene Therapy:

A fusion protein of the invention may also be employed in accordance with the present invention by expression of such fusion protein in vivo, which is often referred to as "gene therapy". Thus, for example, cells may be engineered with a polynucleotide (DNA or RNA) encoding for the fusion protein ex vivo, the engineered cells are then provided to a patient to be treated with the fusion protein. Such methods are well-known in the art. For example, cells may be engineered by procedures known in the art by use of a retroviral particle containing RNA encoding for the fusion protein of the present invention.

Local delivery of the anticoagulant fusion proteins of the present invention using gene therapy may provide the therapeutic agent to the target area, the endothelial cells lining blood vessels.

Both in vitro and in vivo gene therapy methodologies are contemplated. Several methods for transferring potentially therapeutic genes to defined cell populations are known. See, e.g., Mulligan (1993) Science 260:926-931. These methods include:

1) Direct gene transfer. Se, e.g., Wolff et al. (1990) Science 247: 1465-1468;
2) Liposome-mediated DNA transfer. See, e.g., Caplen et al. (1995) Nature Med. 3:39-46; Crystal (1995) Nature Med. 1:15-17; Gao and Huang (1991) Biochem. Biophys. Res. Comm. 179:280-285;
3) Retrovirus-mediated DNA transfer. See, e.g., Kay et al. (1993) Science 262:117-119; Anderson (1992) Science 256:808-813.
4) DNA Virus-mediated DNA transfer. Such DNA viruses include adenoviruses (preferably Ad2 or Ad5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al. (1994) Gene Therapy 1:367-384; U.S. Pat. No. 4,797, 368, incorporated herein by reference, and U.S. Pat. No. 5,139,941, incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity. However, recent developments in the field of lentiviral vectors may circumvent some of these limitations. See Naldini et al. (1996) Science 272:263-267.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Adenoviruses have the advantage that they have a broad host range, can infect quiescent or terminally differentiated cells, such as neurons or hepatocytes, and appear essentially non-oncogenic. See, e.g., Ali et al. (1994), supra, p. 367. Adenoviruses do not appear to integrate into the host genome. Because they exist extrachromosomally, the risk of insertional mutagenesis is greatly reduced. Ali et al. (1994), supra, p. 373.

Adeno-associated viruses exhibit similar advantages as adenoviral-based vectors. However, AAVs exhibit site-specific integration on human chromosome 19 (Ali et al. (1994), supra, p. 377).

In a preferred embodiment, the DNA encoding the fusion proteins of this invention is used in gene therapy for disorders including, but not limited to, deep vein thrombosis, disseminated intravascular coagulation, acute coronary syndrome or cancer with evidence of coagulopathy.

According to this embodiment, gene therapy with DNA encoding the fusion proteins of this invention is provided to a patient in need thereof, concurrent with, or immediately after diagnosis.

The skilled artisan will appreciate that any suitable gene therapy vector containing DNA encoding the fusion protein of the invention or DNA encoding analogs, fragments, derivatives or variants of the fusion protein of the invention may be used in accordance with this embodiment. The techniques for constructing such a vector are known. See, e.g., Anderson, W. F. (1998) *Nature* 392:25-30; Verma I. M. and Somia, N. (1998) *Nature* 389:239-242. Introduction of the fusion protein DNA-containing vector to the target site may be accomplished using known techniques.

The gene therapy vector includes one or more promoters. Suitable promoters which may be employed include, but are not limited to, the retroviral LTR; the SV40 promoter; and the human cytomegalovirus (CVM) promoter described in Miller et al. (1989) *Biotechniques* 7(9):980-990, or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the fusion protein of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAl promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoter.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X; VT-19-17-H2, ψCRE, ψCRIP, GP+#-86, GP+envAm12, and DAN cell lines as described in Miller (1990) *Human Gene Therapy* 1:5-14, which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host. The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

A different approach to gene therapy is "transkaryotic therapy" wherein the patient's cells are treated ex vivo to induce the dormant chromosomal genes to produce the protein of interest after reintroduction to the patient. Transkaryotic therapy assumes the individual has a normal complement of genes necessary for activation. Transkaryotic therapy involves introducing a promoter or other exogenous regulatory sequence capable of activating the nascent genes, into the chromosomal DNA of the patients' cells ex vivo, culturing and selecting for active protein-producing cells, and then reintroducing the activated cells into the patient with the intent that they then become fully established. The "gene activated" cells then manufacture the protein of interest for some significant amount of time, perhaps for as long as the life of the patient. U.S. Pat. Nos. 5,641,670 and 5,733,761 disclose in detail this concept, and are hereby incorporated by reference in their entirety.

Kits:

This invention further relates to kits for research or diagnostic purposes. Kits typically include one or more containers containing the single chain antibodies of the present invention. In a preferred embodiment, the kits comprise containers containing single chain antibodies in a form suitable for derivatizing with a second molecule, e.g., TM domain(s) or fragments thereof. In a more preferred embodiment the kits comprise containers containing the fusion proteins of SEQ ID NO:2 or SEQ ID NO:3.

In another embodiment, the kits may contain DNA sequences encoding the fusion proteins. Preferably the DNA sequences encoding these fusion proteins are provided in a plasmid suitable for transfection into and expression by a host cell. The plasmid may contain a promoter (often an inducible promoter) to regulate expression of the DNA in the host cell. The plasmid may also contain appropriate restriction sites to facilitate the insertion of other DNA sequences into the plasmid to produce various fusion proteins. The plasmids may also contain numerous other elements to facilitate cloning and expression of the encoded proteins. Such elements are well known to those of skill in the art and include, for example, selectable markers, initiation codons, termination codons, and the like.

Therapeutic Indications:

Diseases in which thrombus formation play a significant etiological role include myocardial infarction, disseminated intravascular coagulation, deep vein thrombosis, pulmonary embolism, ischaemic stroke, septic shock, acute respiratory distress syndrome, unstable angina and other arterial and venous occlusive conditions. The fusion proteins of this invention are useful in all of these, as well as in other diseases in which thrombus formation is pathological. Other pathological conditions where the fusion protein of this invention may be useful include cancer with coagulopathy and inflammation. The compounds may also find use in skin and vein grafts and organ transplants. By useful it is meant that the compounds are useful for treatment, either to prevent disease or to prevent its progression to a more severe state. The compounds of this invention also provide a safe and effective anticoagulant, for example, in patients receiving bioprostheses such as heart valves. These compounds may replace heparin and warfarin in the treatment of, for example, pulmonary embolism or acute myocardial infarction. The fusion proteins of this invention may also find use in coating medical devices where coagulation is an issue of concern.

Assays:

A number of laboratory assays for measuring the TM activity of a fusion protein of the invention are available. Protein C activity can be measured in the assay described by Salem, H. H. et al. (1984), supra, and Galvin, J. B. et al. (1987) *J. Biol. Chem.* 262(5):2199-2205. In brief, the assay consists of two steps. The first step is the incubation of the test fusion protein with thrombin and protein C under defined conditions. In the second step, the thrombin is inactivated with hirudin or antithrombin III and heparin, and the activity of the newly activated protein C is determined by the used of a chromogenic substrate, whereby the chromophore is released by the proteolytic activity of activated protein C. This assay is carried out with the purified reagents.

Alternately, the effect of a fusion protein can be measured using plasma clotting time assays such as the activated partial thromboplastin time (APTT), thrombin clotting time (TCT) and/or prothrombin time (PT). These assays distinguish between different mechanisms of coagulation inhibition, and involve the activation of protein C. Prolongation of the clotting time in any one of these assays demonstrates that the molecule can inhibit coagulation in plasma.

The above assays are used to identify fusion proteins with TM activity which are able to bind thrombin and to activate protein C in both purified systems and in a plasma milieu. Further assays are then used to evaluate other activities of native TM such as inhibition of thrombin catalyzed formation of fibrin from fibrinogen (Jakubowski, H. V. et al. (1986) *J. Biol. Chem.* 261(8): 3876-3882), inhibition of thrombin activation of factor V (Esmon, C. T. et al. (1982). *J. Biol. Chem.* 257(14):7944-7947), accelerated inhibition of thrombin by antithrombin III and heparin cofactor II (Esmon, N. L. et al. (1983) *J. Biol. Chem.* 258(20):12238-12242), inhibition of thrombin activation of factor XIII (Polgar, J. et al. (1987) *Thromb. Haemost.* 58(1):140), inhibition of thrombin mediated inactivation of protein S (Thompson, E. A. and Salem, H. H. (1986) *J. Clin. Inv.* 78(1):13-17), and inhibition of thrombin mediated platelet activation and aggregation (Esmon, N. L. et al. (1983), supra).

The following assays, described in detail below in Example 5, are used to measure the in vitro potency of the fusion proteins of the invention: 1) protein C activation assay (chromogenic); 2) sTF/FVIIa activation assay; 3) Factor X activation assay; and 4) protein C activation assay (on TF-rich surface).

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of the example, it should be kept clearly in mind that other and different embodiments of the methods disclosed according to the present invention will no doubt suggest themselves to those of skill in the relevant art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure(s) of all applications, patents and publications, cited above are hereby incorporated by reference.

The following examples are provided as a guide to assist in the practice of the invention, and are not intended as a limitation on the scope of the invention.

EXAMPLE 1

Single Chain Anti-TF Antibody Construct
scFv(TF)3e10

```
(-18) M L G V L V L G A L A L A G L V F P E M A Q
      V N L R E S G G T L V Q P G G S L R L S C A A S
      G F S F T D A W M S W V R Q A P G K E L E W V S
      S I S G S G G S T Y Y A G S V K G R F T I S R D
      N S K N T L Y L Q M N S L R A E D T A V Y Y C A
   20 R V L S L T D Y Y W Y G M D V W G Q G T L V T V
      S A G G G G S G A P N F M L T Q P H S V S A S P
      G K T V T I S C T R S S G S V A S Y Y V Q W Y Q
      Q R P G S S P T T V I Y E D N H R P S G V P D R
      F S G S I D T S S N S A S L T I S G L K T E D E
      A D Y Y C Q S Y D S N N L V V F G G G T K L T V
      L G A A A G A P V P Y P D P L E P R A A (264)
```

The single chain anti-TF antibody scFv(TF)3e10 (SEQ ID NO:1) consists of a signal peptide (−18 to −1), $V_H$ domain (1 to 126), $V_H$-$V_L$ linker (127 to 131), $V_L$ domain (132 to 246), and e-tag sequence (247 to 264).

EXAMPLE 2

Fusion Protein Construct 1 scFv(TF)3e10-TMi456

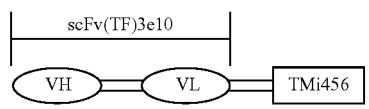

```
(-18) M L G V L V L G A L A L A G L V F P E M A Q
      V N L R E S G G T L V Q P G G S L R L S C A A S
      G F S F T D A W M S W V R Q A P G K E L E W V S
      S I S G S G G S T Y Y A G S V K G R F T I S R D
      N S K N T L Y L Q M N S L R A E D T A V Y Y C A
      R V L S L T D Y Y W Y G M D V W G Q G T L V T V
      S A G G G G S G A P N F M L T Q P H S V S A S P
      G K T V T I S C T R S S G S V A S Y Y V Q W Y Q
      Q R P G S S P T T V I Y E D N H R P S G V P D R
      F S G S I D T S S N S A S L T I S G L K T E D E
```

-continued

```
A  D  Y  Y  C  Q  S  Y  D  S  N  N  L  V  V  F  G  G  G  T  K  L  T  V
L  G  A  A  A  G  G  G  S  G  G  G  G  S  G  G  G  G  S  V  E  P  V
D  P  C  F  R  A  N  C  E  Y  Q  C  Q  P  L  N  Q  T  S  Y  L  C  V  C
A  E  G  F  A  P  I  P  G  E  P  H  R  C  Q  L  F  C  N  Q  T  A  C  P
A  D  C  D  P  N  T  Q  A  S  C  E  C  P  E  G  Y  I  L  D  D  G  F  I
C  T  D  I  D  E  C  E  N  G  G  F  C  S  G  V  C  H  N  L  P  G  T  F
E  C  I  C  G  P  D  S  A  L  A  G  Q  I  G  T  D  C  A  A  A  G  A  P
V  P  Y  P  D  P  L  E  P  R  A  A  (400)
```

The scFv(TF)3e10-TMi456 fusion protein (SEQ ID NO:2) consists of a signal peptide (−18 to −1), $V_H$ domain (1 to 126), $V_H$-$V_L$ linker (127 to 131), $V_L$ domain (132 to 246), $V_L$-TM linker (247 to 264), TMi456 domain (265 to 382), and e-tag sequence (383 to 400). The H381G, M388L, R456G and H457Q mutations in TMi456 are underlined.

EXAMPLE 3

Fusion Protein Construct 2 scFv(TF)3e10-TMi456Δ

```
(-18) M  L  G  V  L  V  L  G  A  L  A  L  A  G  L  V  F  P  E  M  A  Q
V  N  L  R  E  S  G  G  T  L  V  Q  P  G  G  S  L  R  L  S  C  A  A  S
G  F  S  F  T  D  A  W  M  S  W  V  R  Q  A  P  G  K  E  L  E  W  V  S
S  I  S  G  S  G  G  S  T  Y  Y  A  G  S  V  K  G  R  F  T  I  S  R  D
N  S  K  N  T  L  Y  L  Q  M  N  S  L  R  A  E  D  T  A  V  Y  Y  C  A
R  V  L  S  L  T  D  Y  Y  W  Y  G  M  D  V  W  G  Q  G  T  L  V  T  V
S  A  G  G  G  G  S  N  F  M  L  T  Q  P  H  S  V  S  A  S  P  G  K  T
V  T  I  S  C  T  R  S  S  G  S  V  A  S  Y  Y  V  Q  W  Y  Q  Q  R  P
G  S  S  P  T  T  V  I  Y  E  D  N  H  R  P  S  G  V  P  D  R  F  S  G
S  I  D  T  S  S  N  S  A  S  L  T  I  S  G  L  K  T  E  D  E  A  D  Y
Y  C  Q  S  Y  D  S  N  N  L  V  V  F  G  G  G  T  K  L  T  V  L  G  A
A  A  G  G  G  G  S  G  G  G  G  S  G  G  G  G  S  V  E  P  V  D  P  C
F  R  A  N  C  E  Y  Q  C  Q  P  L  N  Q  T  S  Y  L  C  V  C  A  E  G
F  A  P  I  P  G  E  P  H  R  C  Q  L  F  C  N  Q  T  A  C  P  A  D  C
D  P  N  T  Q  A  S  C  E  C  P  E  G  Y  I  L  D  D  G  F  I  C  T  D
I  D  E  C  E  N  G  G  F  C  S  G  V  C  H  N  L  P  G  T  F  E  C  I
C  G  P  D  S  A  L  A  G  Q  I  G  T  D  C  (379)
```

The scFv(TF)3e10-TMi456Δ fusion protein (SEQ ID NO:3) consists of a signal peptide (−18 to −1), $V_H$ domain (1 to 126), $V_H$-$V_L$ linker (127 to 131), $V_L$ domain (132 to 243), $V_L$-TM linker (244 to 261), and TMi456 domain (262 to 379). The H381 G, M388L, R456G and H457Q mutations in TMi456 are underlined.

EXAMPLE 4

Expression of the Fusion Protein in Bacterial/Mammalian Cells

Bacterial expression was possible, but it yielded a protein that had a much reduced TM cofactor activity. The fusion protein was expressed in CHO cells. The expression plasmid contains both the hygromycin B and DHFR selection markers. Original selection was done in 400 μg/ml hygromycin to select a population. The resulting population was then subjected to 100 nM methotrexate selection. During this selection, cells that have amplified copies of the region of DNA containing the selection marker, and target gene, are selected from amongst the population. The expression levels were increased from approximately 0.3 mg/L to about 6 mg/L as a result of this selection.

EXAMPLE 5

In Vitro Assays

1. Protein C Activation Assay (Chromogenic)

This assay was performed by mixing 20 μl each of the following proteins in a microtiter plate: TM sample (unknown or standard), thrombin (3 nM), and protein C (1.5 μM). The assay diluent for each protein was 20 mM Tris-HCl, 0.1M NaCl, 2.5 mM $CaCl_2$, 2.5 mg/ml BSA, pH 7.4. The wells were incubated for 2 hours at 37° C. after which protein C activation was terminated by the addition of 20 μl of hirudin (0.16 unit/μl 370 nM) in assay diluent and incubation for an additional 10 minutes.

The amount of activated protein C formed was detected by adding 100 μl of 1 mM S2266 (in assay diluent), and continuing to incubate the plate at 37° C. The absorbance at 405 nm in each well was read every 10 seconds for 30 minutes, using a Molecular Devices plate reader. The absorbance data was stored, and the change in absorbance per second (slope) in each well was calculated. The change absorbance per second is proportional to pmol/ml of activated protein C.

This ratio was determined empirically using varying concentrations of totally activated protein C. Samples containing 100% activated protein C were generated by mixing protein C at 0 to 1.5 μM with 60 nM rabbit TM and 30 nM thrombin, incubating for 0 to 4 hours, adding hirudin and measuring S2266 activity as above. Conditions under which 100% of the protein C was activated were defined as those in which the S2266 activity (A405/sec) reached plateau.

A unit of activity is defined as 1 pmole of activated protein C generated per ml/min under the reagent conditions defined above. Alternatively, activity values are reported in comparison to native detergent solubilized rabbit TM.

2. sTF/FVIIa Activation Assay

The principle of this assay is depicted below. The tripeptide p-nitroanilide amide bond of the substrate is hydrolyzed by the sTF/FVIIa complex. The liberated chromophore product, p-nitroanilide, is monitored at 405 nm and the concentration of product formed per unit time is calculated using a molar extinction coefficient of 9920 $M^{-1}$ $cm^{-1}$. $IC_{50}$ values (C) are determined by fitting the initial rates into the 4 parameter equation: $Y=(A-D)/(1+(x/C)^B)+D$

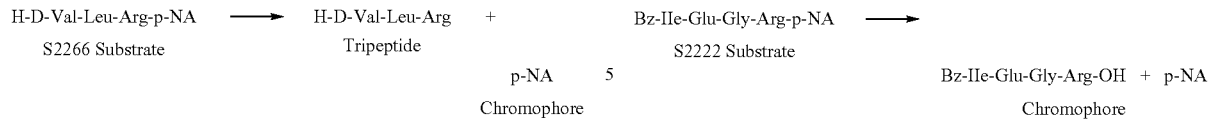

Reagents and Solutions:

1. Assay buffer: 50 mM Tris-HCl, 150 mM NaCl, 5 mM CaCl$_2$, 0.1% BSA, pH7.5
2. Human FVIIa (HCVIIA-0060, Haematologic Technologies Inc.): 10× working solution—prepare 20 nM solution in assay buffer prior to use.
3. Soluble TF (Berlex): 10× working solution—prepare 30 nM solution in assay buffer prior to use.
4. Chromogenic substrate S2266 (Kabi Pharmacia Hepar Inc.): Stock solution: 10 mM in H$_2$O, stored at 4 C. 2.5× working solution—prepare 2.5 mM solution in assay buffer prior to use.
5. Antibody: Prepare 2.5× dilutions in assay buffer prior to use.

Assay Conditions:

Assays are performed in a 96-well microtiter plate at room temperature. The final concentrations of the components are as follows:

| sTF | 3 nM |
|---|---|
| Antibody | vary from 1000 to 0.625 nM |
| FVIIa | 2 nM |
| S2266 | 1 mM |

Assay Procedure:

1. Pipette 0.1 ml of 2.5×AB (or buffer control) into each well.
2. Add 0.025 ml 10×sTF and incubate 10 min at room temperature with mild shaking.
3. Add 0.025 ml 10×FVIIa, incubate 10 min at room temperature with mild shaking.
4. Add 0.1 ml 2.5×S2266 substrate, immediately transfer the plate into a plate reader and measure enzyme kinetics at 405 nm at 10 seconds interval for 15 min.

3. Factor X Activation Assay:

The principle of this assay is depicted below. FVIIa is incubated with recombinant human TF vesicles to form a protease complex capable of activating the substrate, FX. This complex is formed in the presence (or absence) of different concentrations of antibody, then the substrate FX is introduced and the reaction is allowed to proceed to form the product, active protease FXa, which is capable of hydrolyzing the p-nitroanilide amide bond of the chromogenic substrate S2222. The liberated chromophore product, p-nitroanilide, is monitored at 405 nm and the concentration of product formed per unit time is calculated using a molar extinction coefficient of 9920 M$^{-1}$ cm$^{-1}$. IC$_{50}$ values (C) are determined by fitting the initial rates into the 4-parameter equation: $Y=(A-D)/(1+(x/C)^B)+D$ Reagents and Solutions:

1. Assay buffer: 50 mM Tris-HCl, 150 mM NaCl, 5 mM CaCl$_2$, 0.1% BSA, pH7.5
2. Human FVIIa (HCVIIA-0031, Haematologic Technologies Inc.): 4× working solution—prepare 100 pM solution in assay buffer prior to use.
3. Recombinant Human TF (reconstituted in our lab from Innovin, Dade): working solution—prepare 1:480 dilution in assay buffer prior to use.
4. Factor X (HCX-0060, Haematologic Technologies Inc.): 4× working solution—prepare 1000 nM solution in assay buffer prior to use.
5. Chromogenic substrate S2222 (Kabi Pharmacia Hepar Inc.):
   Stock solution: 6 mM in H$_2$O, stored at 4 C.
   Working solution—prepare 0.78 mM solution in 3.57 mM EDTA (to stop the reaction), 150 mM NaCl, 50 mM Tris-HCl pH 7.5 prior to use.
6. Antibody:
   Prepare 4× dilutions in assay buffer prior to use.

Assay Conditions:

Assays are performed in a 96-well microtiter plate at room temperature. The final concentrations of the components are as follows:

| rTF vesicles | ¼ of 1:480 dilution |
|---|---|
| Antibody | vary from 1000 to 0.625 nM |
| FVIIa | 25 pM |
| FX | 250 nM |
| S2222 | 0.546 mM |

Assay Procedure:

1. Pipette 0.015 ml of 4×AB (or buffer control) into each well.
2. Add 0.015 ml 4×rTF vesicles.
3. Add 0.015 ml 4×FVIIa, incubate 10 min at room temperature with mild shaking.
4. Add 0.015 ml 4×FX, incubate 5 min at room temperature with mild shaking.
5. Add 0.14 ml S2222 substrate, immediately transfer the plate into a plate reader and measure enzyme kinetics at 405 nm at 10 seconds interval for 15 minutes.

4. Protein C Activation Assay (on TF-Rich Surface)

This assay is performed as for the chromogenic protein C activation assay listed above with the exception that in this assay human TF-containing PC/PS vesicles are added to the fusion protein, or control TM, before adding the thrombin and protein C.

EXAMPLE 6

Characteristics of the Anti-TF Antibodies

Figure 2:
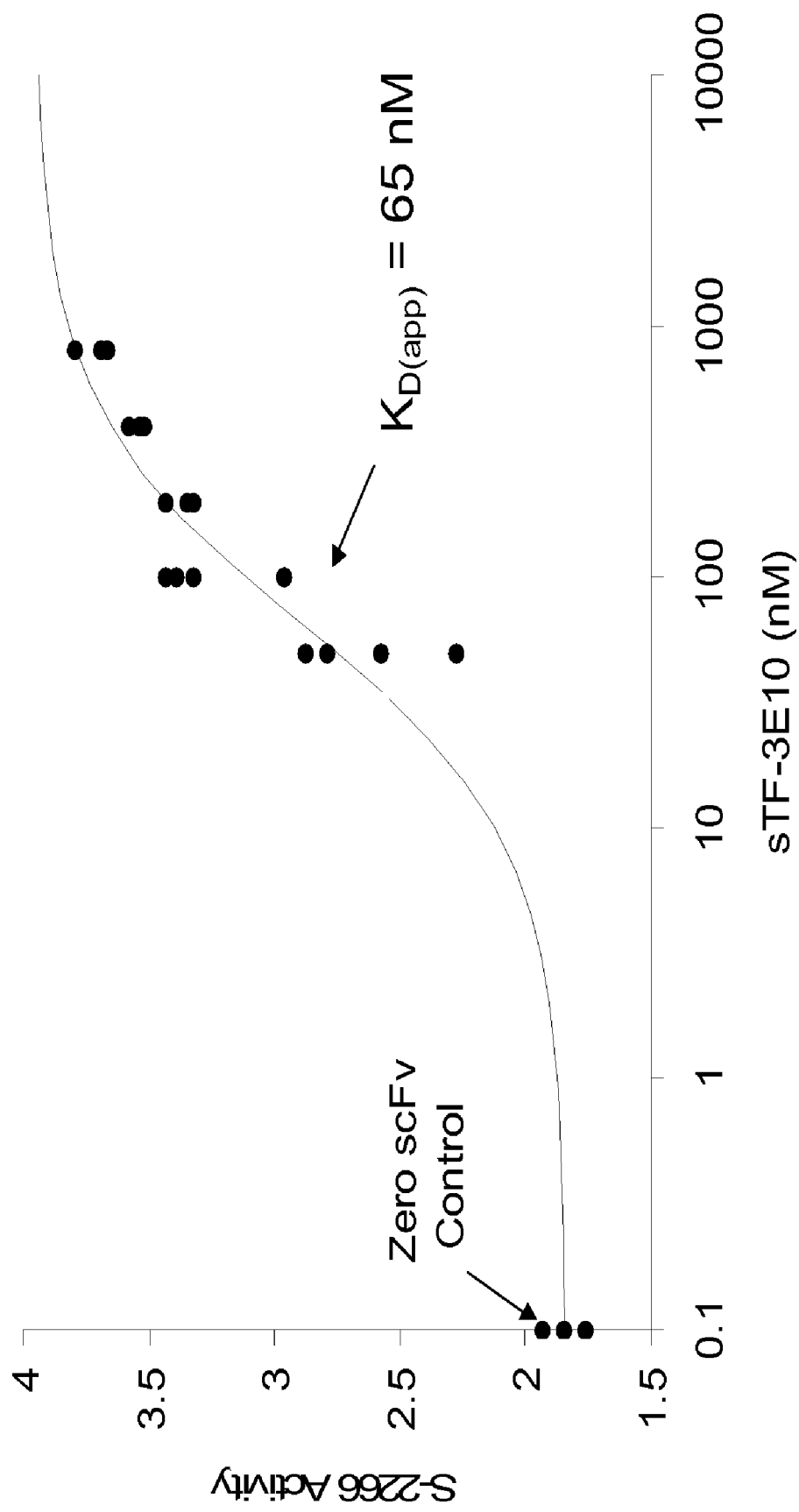
Figure 3:
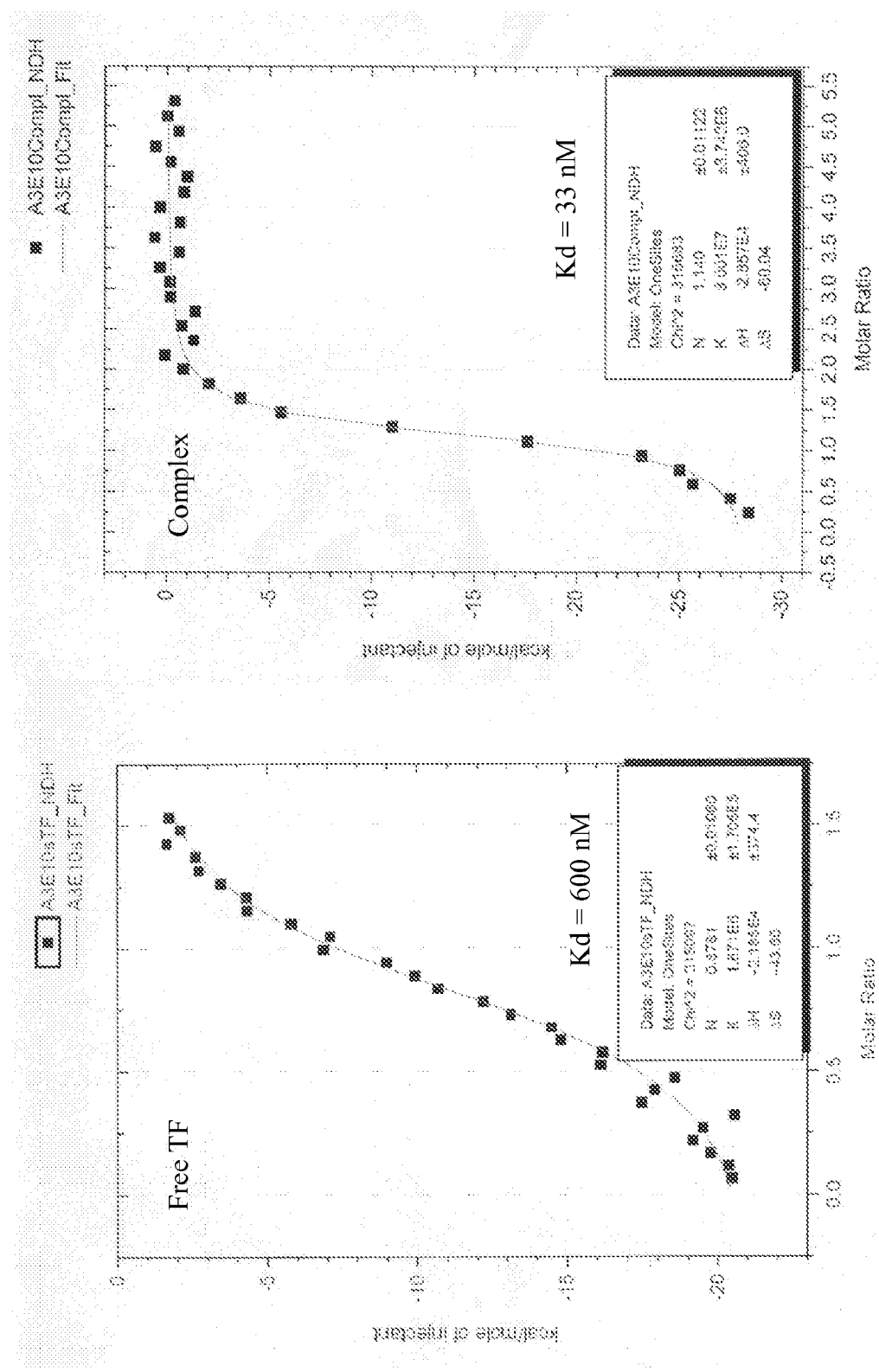
Figure 4:
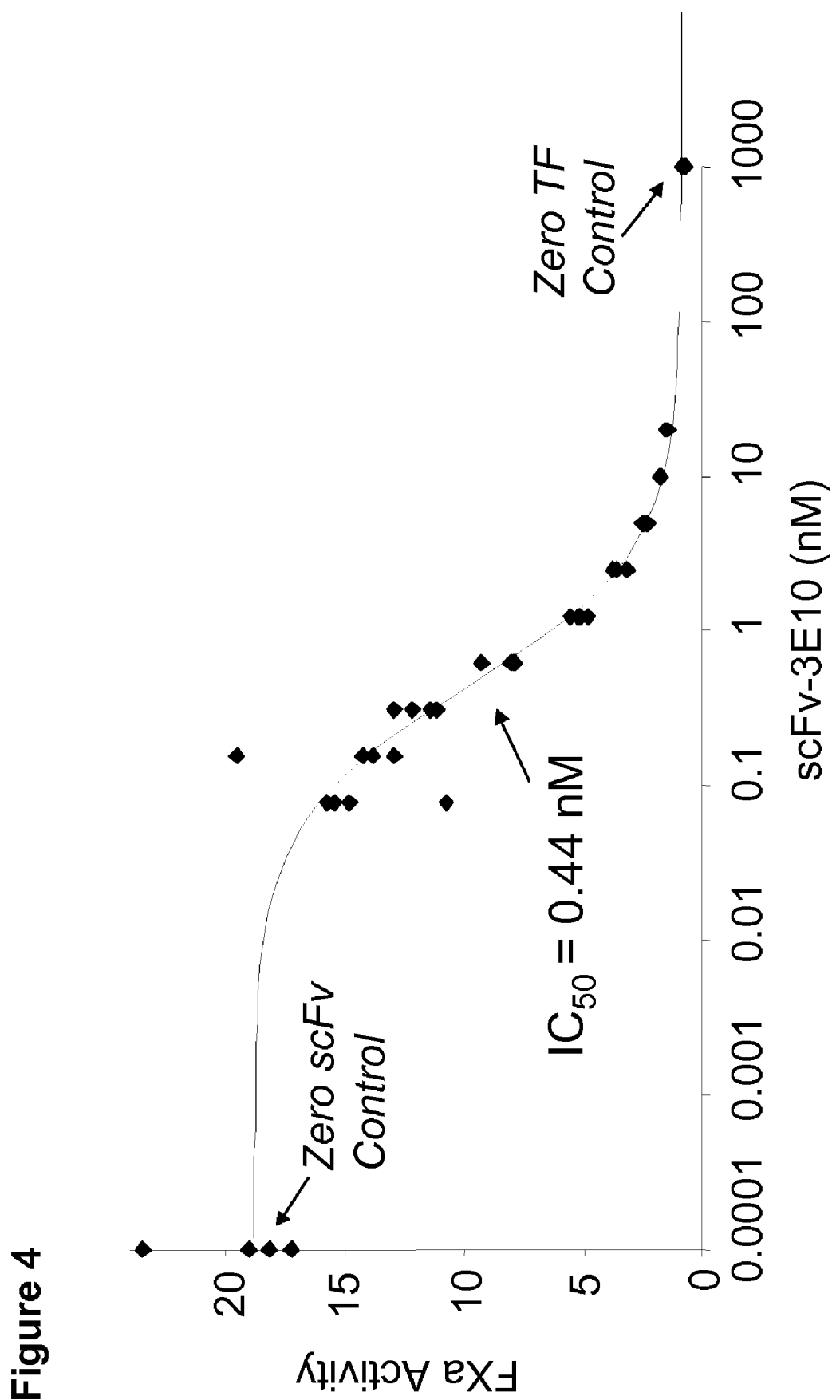
Figure 5:
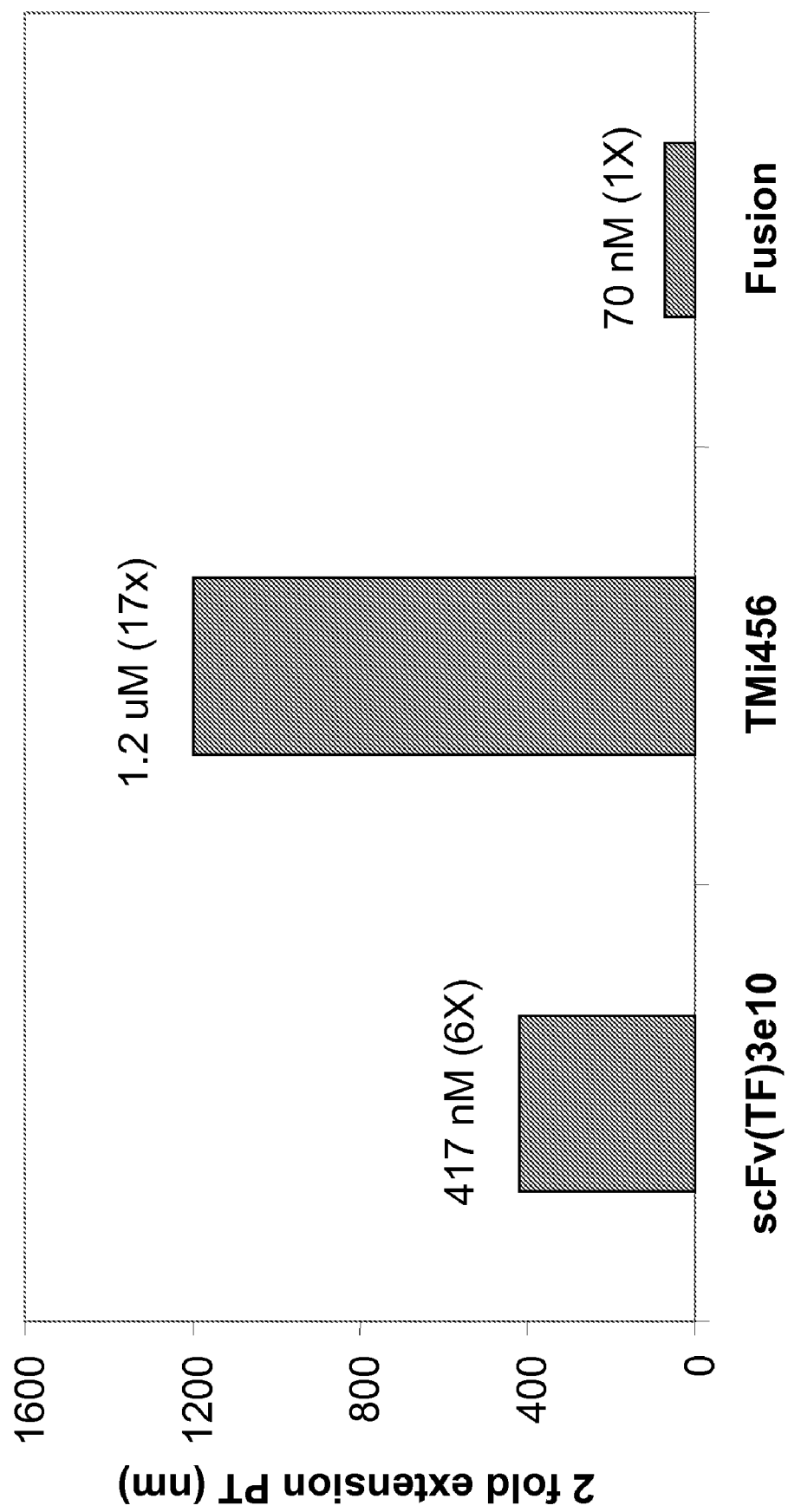

Seven different TF-binding antibodies were isolated from a fully human single chain antibody phage display library. The affinities of the sTF binding antibodies, measured using the BIAcore, were between 35 and 470 nM. The sTF/VIIa assay was used to determine if the antibodies would block the formation of an active VIIa/TF complex. In the sTF/VIIa assay, binding of VIIa to sTF accelerates the rate of cleavage against the chromogenic peptide substrate S2266 by >20-fold. Antibodies that inhibit binding of FVIIa to TF block this acceleration. From among seven different antibodies isolated, only one of them, scFv(TF)3e10, did not inhibit the sTF/VIIa assay. This antibody increased the affinity of FVIIa for sTF, decreasing the $K_D$ 5-fold (FIG. 1). The $K_D$ of the scFv(TF)3e10 antibody for sTF, measured using the sTF/FVIIa assay, was 65.4 nM (FIG. 2). Microcalorimetry was used to compare the affinity of scFv(TF)3e10 for TF as compared to the FVIIa/TF complex. These experiments revealed that the antibody has a 20-fold higher affinity for the TF/FVIIa complex as compared to free sTF (33 nM vs. 600 nM, FIG. 3). The antibodies were compared using the FX activation assay, which consists of full length TF in phospholipid vesicles, FVIIa and FX. The amount of FXa generated is determined using the chromogenic substrate S2765. Although the scFv(TF)3e10 antibody did not have the highest affinity as measured by BIAcore and it increased the affinity of FVIIa for sTF, it was the only antibody in the group that inhibited FX activation and prolonged the clotting time in the PT assay. The $IC_{50}$ of the scFV(TF)3e10 (dimer) antibody for inhibition in the FX activation assay was 0.44 nM (FIG. 4) and a two-fold extension of PT occurred at 417 nM (FIG. 5).

The scFv(TF)3e10 antibody was identified on the basis of binding to recombinant human soluble TF. The sequence homology of TF between the human and murine or human and rabbit is 58% and 71%, respectively. The antibody binds to a unique epitope on human TF that interferes with activation of FX by the FVIIa/TF complex. Physiologically, the antibody has an advantage over antibodies that compete with FVII or FVIIa binding to TF. The $K_D$ of both FVII and FVIIa in human plasma is 10 nM, or between 100- and 1000-fold greater than the $K_D$. The off-rate for the high affinity complex will be slow (70 to 700 seconds, assuming $k_{on}=10^8$ $M^{-1}$ $sec^{-1}$). In contrast, the Km of FX for the VIIa/TF complex is between 0.200 to 4 µM and the concentration of FX in human plasma is 130 nM (between 0.03- and 0.65-fold $K_D$). The primary function of the FVIIa/TF complex in coagulation is to convert FX to FXa.

EXAMPLE 7

In Vitro Characteristics of the Fusion Protein scFv(TF)3e10-TMi456

Figure 6:
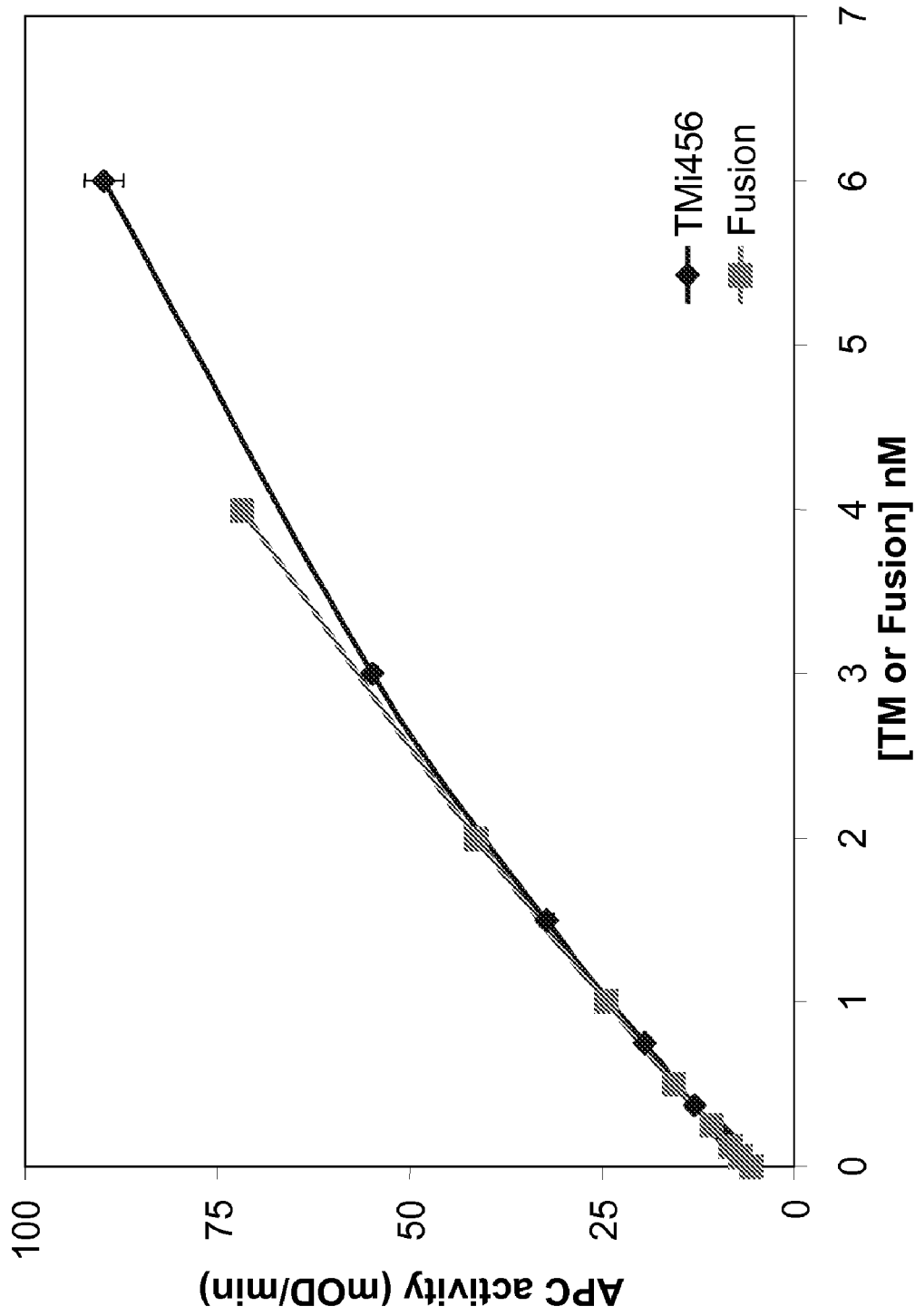

The characteristics of a fusion protein of the invention, scFv(TF)3e10-TMi456, was assessed in a variety of in vitro assays. The fusion protein, scFv(TF)3e10-TMi456, retained the ability of inhibit FX activation by the FVIIa/TF complex ($IC_{50}$=0.5 nM, data not shown) and acted as a cofactor for the thrombin catalyzed activation of protein C (chromogenic assay, FIG. 6). No significant difference in TM cofactor activity was observed between the fusion protein and Tmi456 alone in the absence of TF-containing phospholipid vesicles. In contrast, the TM cofactor activity of the fusion protein, but not TMi456, was enhanced >5-fold in the presence of TF-containing phospholipid vesicles (FIG. 7). The in vitro potency of the fusion protein, scFv(TF)3e10-TMi456, against TF-induced coagulation (PT assay, extrinsic coagulation pathway) was 6-fold better than the scFv(TF)3e10 antibody and 17-fold better than TMi456 alone (FIG. 5). In contrast, the in vitro potency of the fusion protein against the intrinsic and common coagulation pathways was not significantly affected (APTT and TCT assays, data not shown). Therefore, the dose of fusion protein that caused a two-fold extension in the PT had only a modest effect on the APTT, whereas TMi456, at an equivalent dose in the PT, caused a 4-fold enhancement in the APTT (FIG. 8). This in vitro profile is consistent with that expected for TF/FVIIa-directed anticoagulants that are known to have superior efficacy to bleeding ratios in animal models of thrombosis. In agreement with the plasma-based coagulation assays, the fusion protein scFv(TF)3e10-TMi456 was more potent in a TF-induced whole blood coagulation assay (Thromboelastograph, TEG) than either scFv(TF)3e10 or Tmi456 alone (FIG. 9). In addition, the fusion protein scFv(TF)3e10-TMi456 had a more predictable dose response in the TF-induced whole blood coagulation assay than low molecular weight heparin (LMWH, FIG. 10). In summary, the above data demonstrate that the fusion proteins of the invention are potent and selective anticoagulants in vitro.

EXAMPLE 8

In Vivo Rat Thromboembolism Model

The TF antibody portion of the fusion protein scFv(TF)3e10-TMi456, is specific for primate TF. A thromboembolism model triggered by human TF (thromboplastin reagent containing human recombinant TF, Ortho) was developed in conscious male Sprague-Dawley rats (350-400 g, n>7/group). In this model of disseminated intravascular coagulation (DIC), TF, via thromboplastin injection, induces pulmonary fibrin deposition, respiratory failure, and death. Equimolar doses of scFv(TF)3e10-TMi456 or scFv(TF)3e10, or vehicle were injected into the tail vein followed, 15 min later, by a bolus injection of thromboplastin (0.5 ml/kg). In the vehicle treated group, this dose of TF resulted in 60% lethality ($LD_{60}$), usually within 5 min after thromboplastin injection. The rats were scored according to the following morbidity-mortality scoring system: 0=unaffected; 1=mild respiratory distress (recover within 30 min); 2=severe respiratory distress (moribund, recovery required more than 60 min); and 3=death. The average score was used for comparing the efficacy of the 4 different treatment groups. The results using this in vivo assay are depicted in FIG. 11. The fusion protein of the invention was able to inhibit death and respiratory distress in this assay.

The preceding examples can be repeated with similar success by substituting the generically or specifically described reactants and/or operating conditions of this invention for those used in the preceding examples.

While the invention has been illustrated with respect to the production of certain fusion protein constructs, it is apparent that variations and modifications of the invention can be made without departing from the spirit or scope of the invention.

What is claimed is:

1. A method for protecting against thrombus formation, comprising administering a therapeutically effective amount of an anticoagulant fission protein, comprising a targeting protein that interacts with tissue factor (TF) or the factor VIIa/TF (FVIIa/TF) complex, which is operably linked to the thrombomodulin (TM) EGF456 domain and the interdomain loop between EGF3 and EGF4, wherein said fusion protein inhibits the generation of thrombin without directly affecting other coagulation parameters such as the activation and aggregation of platelets and wherein said fusion protein comprises the amino acid sequence of SEQ ID NO:2 or SEQ ID NO:3.

2. The method of claim 1, wherein said method is to protect against thrombus formation in ischemic stroke, thrombotic complications following angioplasty, or microvascular surgery.

3. A method for inhibiting coagulation associated with deep vein thrombosis (DVT), disseminated intravascular coagulation (DIC), acute coronary syndrome, or cancer in a patient, comprising administering a therapeutically effective amount of an anticoagulant fusion protein, comprising a targeting protein that interacts with tissue factor (TF) or the factor VIIa/TF (FVIIa/TF) complex, which is operably linked to the thrombomodulin (TM) EGF456 domain and the interdomain loop between EGF3 and EGF4 to said patient, wherein said fusion protein comprises the amino acid sequence of SEQ ID NO:2 or SEQ ID NO:3.

4. A method for inhibiting the inflammatory response in a patient, comprising administering a therapeutically effective amount of an anticoagulant fusion protein, comprising a targeting protein that interacts with tissue factor (IF) or the factor VIIa/TF (FVIIa/TF) complex, which is operably linked to the thrombomodulin (TM) EGF456 domain and the interdomain loop between EGF3 and EGF4 to said patient, wherein said fusion protein comprises the amino acid sequence of SEQ ID NO:2 or SEQ ID NO:3.

5. The method of claim 4, wherein said inflammatory response is associated with sepsis, skin and vein grafts, or organ transplants.

* * * * *

SEQUENCE LISTING

<160> NUMBER OF SEQ ID NOS: 5

<210> SEQ ID NO 1
<211> LENGTH: 282
<212> TYPE: PRT
<213> ORGANISM: artificial
<220> FEATURE:
<223> OTHER INFORMATION: scFv(TF)3e10

<400> SEQUENCE: 1

Met Leu Gly Val Leu Val Leu Gly Ala Leu Ala Leu Ala Gly Leu Val
1               5                   10                  15

Phe Pro Glu Met Ala Gln Val Asn Leu Arg Glu Ser Gly Gly Thr Leu
            20                  25                  30

Val Gln Pro Gly Gly Ser Leu Arg Leu Ser Cys Ala Ala Ser Gly Phe
        35                  40                  45

Ser Phe Thr Asp Ala Trp Met Ser Trp Val Arg Gln Ala Pro Gly Lys
    50                  55                  60

Glu Leu Glu Trp Val Ser Ser Ile Ser Gly Ser Gly Ser Thr Tyr
65                  70                  75                  80

Tyr Ala Gly Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Val Leu Ser Leu Thr Asp Tyr Tyr Trp
        115                 120                 125

Tyr Gly Met Asp Val Trp Gly Gln Gly Thr Leu Val Thr Val Ser Ala
    130                 135                 140

Gly Gly Gly Gly Ser Gly Ala Pro Asn Phe Met Leu Thr Gln Pro His
145                 150                 155                 160

Ser Val Ser Ala Ser Pro Gly Lys Thr Val Thr Ile Ser Cys Thr Arg
                165                 170                 175

Ser Ser Gly Ser Val Ala Ser Tyr Tyr Val Gln Trp Tyr Gln Gln Arg
            180                 185                 190

Pro Gly Ser Ser Pro Thr Thr Val Ile Tyr Glu Asp Asn His Arg Pro
        195                 200                 205

Ser Gly Val Pro Asp Arg Phe Ser Gly Ser Ile Asp Thr Ser Ser Asn
    210                 215                 220

Ser Ala Ser Leu Thr Ile Ser Gly Leu Lys Thr Glu Asp Glu Ala Asp
225                 230                 235                 240

Tyr Tyr Cys Gln Ser Tyr Asp Ser Asn Asn Leu Val Val Phe Gly Gly
                245                 250                 255

Gly Thr Lys Leu Thr Val Leu Gly Ala Ala Gly Ala Pro Val Pro
            260                 265                 270

Tyr Pro Asp Pro Leu Glu Pro Arg Ala Ala
        275                 280

<210> SEQ ID NO 2
<211> LENGTH: 418
<212> TYPE: PRT
<213> ORGANISM: artificial
<220> FEATURE:
<223> OTHER INFORMATION: fusion protein construct 1

```
<400> SEQUENCE: 2

Met Leu Gly Val Leu Val Leu Gly Ala Leu Ala Leu Ala Gly Leu Val
1               5                   10                  15

Phe Pro Glu Met Ala Gln Val Asn Leu Arg Glu Ser Gly Gly Thr Leu
                20                  25                  30

Val Gln Pro Gly Gly Ser Leu Arg Leu Ser Cys Ala Ala Ser Gly Phe
            35                  40                  45

Ser Phe Thr Asp Ala Trp Met Ser Trp Val Arg Gln Ala Pro Gly Lys
    50                  55                  60

Glu Leu Glu Trp Val Ser Ser Ile Ser Gly Ser Gly Ser Thr Tyr Tyr
65                  70                  75                  80

Tyr Ala Gly Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Val Leu Ser Leu Thr Asp Tyr Tyr Trp
        115                 120                 125

Tyr Gly Met Asp Val Trp Gly Gln Gly Thr Leu Val Thr Val Ser Ala
    130                 135                 140

Gly Gly Gly Gly Ser Gly Ala Pro Asn Phe Met Leu Thr Gln Pro His
145                 150                 155                 160

Ser Val Ser Ala Ser Pro Gly Lys Thr Val Thr Ile Ser Cys Thr Arg
                165                 170                 175

Ser Ser Gly Ser Val Ala Ser Tyr Tyr Val Gln Trp Tyr Gln Gln Arg
            180                 185                 190

Pro Gly Ser Ser Pro Thr Thr Val Ile Tyr Glu Asp Asn His Arg Pro
        195                 200                 205

Ser Gly Val Pro Asp Arg Phe Ser Gly Ser Ile Asp Thr Ser Ser Asn
    210                 215                 220

Ser Ala Ser Leu Thr Ile Ser Gly Leu Lys Thr Glu Asp Glu Ala Asp
225                 230                 235                 240

Tyr Tyr Cys Gln Ser Tyr Asp Ser Asn Asn Leu Val Val Phe Gly Gly
                245                 250                 255

Gly Thr Lys Leu Thr Val Leu Gly Ala Ala Ala Gly Gly Gly Gly Ser
            260                 265                 270

Gly Gly Gly Gly Ser Gly Gly Gly Ser Val Glu Pro Val Asp Pro
        275                 280                 285

Cys Phe Arg Ala Asn Cys Glu Tyr Gln Cys Gln Pro Leu Asn Gln Thr
    290                 295                 300

Ser Tyr Leu Cys Val Cys Ala Glu Gly Phe Ala Pro Ile Pro Gly Glu
305                 310                 315                 320

Pro His Arg Cys Gln Leu Phe Cys Asn Gln Thr Ala Cys Pro Ala Asp
                325                 330                 335

Cys Asp Pro Asn Thr Gln Ala Ser Cys Glu Cys Pro Glu Gly Tyr Ile
            340                 345                 350

Leu Asp Asp Gly Phe Ile Cys Thr Asp Ile Asp Glu Cys Glu Asn Gly
        355                 360                 365

Gly Phe Cys Ser Gly Val Cys His Asn Leu Pro Gly Thr Phe Glu Cys
    370                 375                 380

Ile Cys Gly Pro Asp Ser Ala Leu Ala Gly Gln Ile Gly Thr Asp Cys
385                 390                 395                 400
```

Ala Ala Ala Gly Ala Pro Val Pro Tyr Pro Asp Pro Leu Glu Pro Arg
            405                 410                 415

Ala Ala

<210> SEQ ID NO 3
<211> LENGTH: 397
<212> TYPE: PRT
<213> ORGANISM: artificial
<220> FEATURE:
<223> OTHER INFORMATION: Fusion protein construct 2

<400> SEQUENCE: 3

Met Leu Gly Val Leu Val Leu Gly Ala Leu Ala Leu Ala Gly Leu Val
1               5                   10                  15

Phe Pro Glu Met Ala Gln Val Asn Leu Arg Glu Ser Gly Gly Thr Leu
            20                  25                  30

Val Gln Pro Gly Gly Ser Leu Arg Leu Ser Cys Ala Ala Ser Gly Phe
        35                  40                  45

Ser Phe Thr Asp Ala Trp Met Ser Trp Val Arg Gln Ala Pro Gly Lys
    50                  55                  60

Glu Leu Glu Trp Val Ser Ser Ile Ser Gly Ser Gly Ser Thr Tyr
65                  70                  75                  80

Tyr Ala Gly Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Val Leu Ser Leu Thr Asp Tyr Tyr Trp
        115                 120                 125

Tyr Gly Met Asp Val Trp Gly Gln Gly Thr Leu Val Thr Val Ser Ala
    130                 135                 140

Gly Gly Gly Gly Ser Asn Phe Met Leu Thr Gln Pro His Ser Val Ser
145                 150                 155                 160

Ala Ser Pro Gly Lys Thr Val Thr Ile Ser Cys Thr Arg Ser Ser Gly
                165                 170                 175

Ser Val Ala Ser Tyr Tyr Val Gln Trp Tyr Gln Gln Arg Pro Gly Ser
            180                 185                 190

Ser Pro Thr Thr Val Ile Tyr Glu Asp Asn His Arg Pro Ser Gly Val
        195                 200                 205

Pro Asp Arg Phe Ser Gly Ser Ile Asp Thr Ser Ser Asn Ser Ala Ser
    210                 215                 220

Leu Thr Ile Ser Gly Leu Lys Thr Glu Asp Glu Ala Asp Tyr Tyr Cys
225                 230                 235                 240

Gln Ser Tyr Asp Ser Asn Asn Leu Val Val Phe Gly Gly Gly Thr Lys
                245                 250                 255

Leu Thr Val Leu Gly Ala Ala Ala Gly Gly Gly Gly Ser Gly Gly Gly
            260                 265                 270

Gly Ser Gly Gly Gly Gly Ser Val Glu Pro Val Asp Pro Cys Phe Arg
        275                 280                 285

Ala Asn Cys Glu Tyr Gln Cys Gln Pro Leu Asn Gln Thr Ser Tyr Leu
    290                 295                 300

Cys Val Cys Ala Glu Gly Phe Ala Pro Ile Pro Gly Glu Pro His Arg
305                 310                 315                 320

Cys Gln Leu Phe Cys Asn Gln Thr Ala Cys Pro Ala Asp Cys Asp Pro
                325                 330                 335

```
Asn Thr Gln Ala Ser Cys Glu Cys Pro Glu Gly Tyr Ile Leu Asp Asp
                340                 345                 350
Gly Phe Ile Cys Thr Asp Ile Asp Glu Cys Glu Asn Gly Gly Phe Cys
            355                 360                 365
Ser Gly Val Cys His Asn Leu Pro Gly Thr Phe Glu Cys Ile Cys Gly
        370                 375                 380
Pro Asp Ser Ala Leu Ala Gly Gln Ile Gly Thr Asp Cys
385                 390                 395

<210> SEQ ID NO 4
<211> LENGTH: 3466
<212> TYPE: DNA
<213> ORGANISM: homo sapiens
<220> FEATURE:
<221> NAME/KEY: CDS
<222> LOCATION: (151)..(1875)
<220> FEATURE:
<221> NAME/KEY: mat_peptide
<222> LOCATION: (205)..()

<400> SEQUENCE: 4
caggggctgc gcgcagcggc aagaagtgtc tgggctggga cggacaggag aggctgtcgc      60
catcggcgtc ctgtgcccct ctgctccggc acggccctgt cgcagtgccc gcgctttccc     120
cggcgcctgc acgcggcgcg cctgggtaac atg ctt ggg gtc ctg gtc ctt ggc      174
                                 Met Leu Gly Val Leu Val Leu Gly
                                                     -15 gcg ctg gcc ctg gcc ggc ctg ggg ttc ccc gca ccc gca gag ccg cag      222
Ala Leu Ala Leu Ala Gly Leu Gly Phe Pro Ala Pro Ala Glu Pro Gln
-10                  -5                  -1  1               5 ccg ggt ggc agc cag tgc gtc gag cac gac tgc ttc gcg ctc tac ccg      270
Pro Gly Gly Ser Gln Cys Val Glu His Asp Cys Phe Ala Leu Tyr Pro
             10                  15                  20 ggc ccc gcg acc ttc ctc aat gcc agt cag atc tgc gac gga ctg cgg      318
Gly Pro Ala Thr Phe Leu Asn Ala Ser Gln Ile Cys Asp Gly Leu Arg
         25                  30                  35 ggc cac cta atg aca gtg cgc tcc tcg gtg gct gcc gat gtc att tcc      366
Gly His Leu Met Thr Val Arg Ser Ser Val Ala Ala Asp Val Ile Ser
     40                  45                  50 ttg cta ctg aac ggc gac ggc ggc gtt ggc cgc cgg cgc ctc tgg atc      414
Leu Leu Leu Asn Gly Asp Gly Gly Val Gly Arg Arg Arg Leu Trp Ile
55                  60                  65                  70 ggc ctg cag ctg cca ccc ggc tgc ggc gac ccc aag cgc ctc ggg ccc      462
Gly Leu Gln Leu Pro Pro Gly Cys Gly Asp Pro Lys Arg Leu Gly Pro
                 75                  80                  85 ctg cgc ggc ttc cag tgg gtt acg gga gac aac aac acc agc tat agc      510
Leu Arg Gly Phe Gln Trp Val Thr Gly Asp Asn Asn Thr Ser Tyr Ser
             90                  95                 100 agg tgg gca cgg ctc gac ctc aat ggg gct ccc ctc tgc ggc ccg ttg      558
Arg Trp Ala Arg Leu Asp Leu Asn Gly Ala Pro Leu Cys Gly Pro Leu
        105                 110                 115 tgc gtc gct gtc tcc gct gct gag gcc act gtg ccc agc gag ccg atc      606
Cys Val Ala Val Ser Ala Ala Glu Ala Thr Val Pro Ser Glu Pro Ile
    120                 125                 130 tgg gag gag cag cag tgc gaa gtg aag gcc gat ggc ttc ctc tgc gag      654
Trp Glu Glu Gln Gln Cys Glu Val Lys Ala Asp Gly Phe Leu Cys Glu
135                 140                 145                 150 ttc cac ttc cca gcc acc tgc agg cca ctg gct gtg gag ccc ggc gcc      702
Phe His Phe Pro Ala Thr Cys Arg Pro Leu Ala Val Glu Pro Gly Ala
                155                 160                 165
```

```
                                                   -continued gcg gct gcc gcc gtc tcg atc acc tac ggc acc ccg ttc gcg gcc cgc      750
Ala Ala Ala Ala Val Ser Ile Thr Tyr Gly Thr Pro Phe Ala Ala Arg
            170                 175                 180 gga gcg gac ttc cag gcg ctg ccg gtg ggc agc tcc gcc gcg gtg gct      798
Gly Ala Asp Phe Gln Ala Leu Pro Val Gly Ser Ser Ala Ala Val Ala
                185                 190                 195 ccc ctc ggc tta cag cta atg tgc acc gcg ccg cca gcg gtc cag          846
Pro Leu Gly Leu Gln Leu Met Cys Thr Ala Pro Gly Ala Val Gln
    200                 205                 210 ggg cac tgg gcc agg gag gcg ccg ggc gct tgg gac tgc agc gtg gag      894
Gly His Trp Ala Arg Glu Ala Pro Gly Ala Trp Asp Cys Ser Val Glu
215                 220                 225                 230 aac ggc ggc tgc gag cac gcg tgc aat gcg atc cct ggg gct ccc cgc      942
Asn Gly Gly Cys Glu His Ala Cys Asn Ala Ile Pro Gly Ala Pro Arg
                235                 240                 245 tgc cag tgc cca gcc ggc gcc gcc ctg cag gca gac ggg cgc tcc tgc      990
Cys Gln Cys Pro Ala Gly Ala Ala Leu Gln Ala Asp Gly Arg Ser Cys
            250                 255                 260 acc gca tcc gcg acg cag tcc tgc aac gac ctc tgc gag cac ttc tgc     1038
Thr Ala Ser Ala Thr Gln Ser Cys Asn Asp Leu Cys Glu His Phe Cys
            265                 270                 275 gtt ccc aac ccc gac cag ccg ggc tcc tac tcg tgc atg tgc gag acc     1086
Val Pro Asn Pro Asp Gln Pro Gly Ser Tyr Ser Cys Met Cys Glu Thr
        280                 285                 290 ggc tac cgg ctg gcg gcc gac caa cac cgg tgc gag gac gtg gat gac     1134
Gly Tyr Arg Leu Ala Ala Asp Gln His Arg Cys Glu Asp Val Asp Asp
295                 300                 305                 310 tgc ata ctg gag ccc agt ccg tgt ccg cag cgc tgt gtc aac aca cag     1182
Cys Ile Leu Glu Pro Ser Pro Cys Pro Gln Arg Cys Val Asn Thr Gln
                315                 320                 325 ggt ggc ttc gag tgc cac tgc tac cct aac tac gac ctg gtg gac ggc     1230
Gly Gly Phe Glu Cys His Cys Tyr Pro Asn Tyr Asp Leu Val Asp Gly
            330                 335                 340 gag tgt gtg gag ccc gtg gac ccg tgc ttc aga gcc aac tgc gag tac     1278
Glu Cys Val Glu Pro Val Asp Pro Cys Phe Arg Ala Asn Cys Glu Tyr
            345                 350                 355 cag tgc cag ccc ctg aac caa act agc tac ctc tgc gtc tgc gcc gag     1326
Gln Cys Gln Pro Leu Asn Gln Thr Ser Tyr Leu Cys Val Cys Ala Glu
            360                 365                 370 ggc ttc gcg ccc att ccc cac gag ccg cac agg tgc cag atg ttt tgc     1374
Gly Phe Ala Pro Ile Pro His Glu Pro His Arg Cys Gln Met Phe Cys
375                 380                 385                 390 aac cag act gcc tgt cca gcc gac tgc gac ccc aac acc cag gct agc     1422
Asn Gln Thr Ala Cys Pro Ala Asp Cys Asp Pro Asn Thr Gln Ala Ser
                395                 400                 405 tgt gag tgc cct gaa ggc tac atc ctg gac gac ggt ttc atc tgc acg     1470
Cys Glu Cys Pro Glu Gly Tyr Ile Leu Asp Asp Gly Phe Ile Cys Thr
            410                 415                 420 gac atc gac gag tgc gaa aac ggc ggc ttc tgc tcc ggg gtg tgc cac     1518
Asp Ile Asp Glu Cys Glu Asn Gly Gly Phe Cys Ser Gly Val Cys His
            425                 430                 435 aac ctc ccc ggt acc ttc gag tgc atc tgc ggg ccc gac tcg gcc ctt     1566
Asn Leu Pro Gly Thr Phe Glu Cys Ile Cys Gly Pro Asp Ser Ala Leu
        440                 445                 450 gtc cgc cac att ggc acc gac tgt gac tcc ggc aag gtg gac ggt ggc     1614
Val Arg His Ile Gly Thr Asp Cys Asp Ser Gly Lys Val Asp Gly Gly
455                 460                 465                 470 gac agc ggc tct ggc gag ccc ccg ccc agc ccg acg ccc ggc tcc acc     1662
Asp Ser Gly Ser Gly Glu Pro Pro Pro Ser Pro Thr Pro Gly Ser Thr
                475                 480                 485
```

| | | | | | | | | | | | | | | | | |
|---|---|---|---|---|---|---|---|---|---|---|---|---|---|---|---|---|
| ttg | act | cct | ccg | gcc | gtg | ggg | ctc | gtg | cat | tcg | ggc | ttg | ctc | ata | ggc | 1710 |
| Leu | Thr | Pro | Pro | Ala | Val | Gly | Leu | Val | His | Ser | Gly | Leu | Leu | Ile | Gly | |
| | | | 490 | | | | | 495 | | | | | 500 | | | |
| atc | tcc | atc | gcg | agc | ctg | tgc | ctg | gtg | gtg | gcg | ctt | ttg | gcg | ctc | ctc | 1758 |
| Ile | Ser | Ile | Ala | Ser | Leu | Cys | Leu | Val | Val | Ala | Leu | Leu | Ala | Leu | Leu | |
| | | 505 | | | | | 510 | | | | | 515 | | | | |
| tgc | cac | ctg | cgc | aag | aag | cag | ggc | gcc | gcc | agg | gcc | aag | atg | gag | tac | 1806 |
| Cys | His | Leu | Arg | Lys | Lys | Gln | Gly | Ala | Ala | Arg | Ala | Lys | Met | Glu | Tyr | |
| 520 | | | | | 525 | | | | | 530 | | | | | | |
| aag | tgc | gcg | gcc | cct | tcc | aag | gag | gta | gtg | ctg | cag | cac | gtg | cgg | acc | 1854 |
| Lys | Cys | Ala | Ala | Pro | Ser | Lys | Glu | Val | Val | Leu | Gln | His | Val | Arg | Thr | |
| 535 | | | | 540 | | | | | 545 | | | | | 550 | | |

| | | | | | | |
|---|---|---|---|---|---|---|
| gag | cgg | acg | ccg | cag | aga | ctc tgagcggcct ccgtccagga gcctggctcc | 1905 |
| Glu | Arg | Thr | Pro | Gln | Arg | Leu | |
| | | | 555 | | | | |

| | |
|---|---|
| gtccaggagc ctgtgcctcc tcaccccag ctttgctacc aaagcacctt agctggcatt | 1965 |
| acagctggag aagaccctcc ccgcacccc caagctgttt tcttctattc catggctaac | 2025 |
| tggcgagggg gtgattagag ggaggagaat gagcctcggc ctcttccgtg acgtcactgg | 2085 |
| accactgggc aatgatggca attttgtaac gaagacacag actgcgattt gtcccaggtc | 2145 |
| ctcactaccg ggcgcaggag ggtgagcgtt attggtcggc agccttctgg gcagaccttg | 2205 |
| acctcgtggg ctaggatga ctaaaatatt tattttttt aagtatttag gttttttgttt | 2265 |
| gtttcctttg ttcttacctg tatgtctcca gtatccactt tgcacagctc tccggtctct | 2325 |
| ctctctctac aaactcccac ttgtcatgtg acaggtaaac tatcttggtg aattttttt | 2385 |
| tcctagccct ctcacattta tgaagcaagc cccacttatt ccccattctt cctagttttc | 2445 |
| tcctcccagg aactgggcca actcacctga gtcaccctac ctgtgcctga ccctacttct | 2505 |
| tttgctctta gctgtctgct cagacagaac ccctacatga aacagaaaca aaaacactaa | 2565 |
| aaataaaaat ggccatttgc ttttcacca gatttgctaa tttatcctga aatttcagat | 2625 |
| tcccagagca aaataatttt aaacaaaggt tgagatgtaa aaggtattaa attgatgttg | 2685 |
| ctggactgtc atagaaatta cacccaaaga ggtatttatc tttactttta aacagtgagc | 2745 |
| ctgaattttg ttgctgtttt gatttgtact gaaaaatggt aattgttgct aatcttctta | 2805 |
| tgcaattttcc tttttgtta ttattactta ttttgacag tgttgaaaat gttcagaagg | 2865 |
| ttgctctaga ttgcgagaag agacaaacac ctcccaggag acagttcaag aaagcttcaa | 2925 |
| actgcatgat tcatgccaat tagcaattga ctgtcactgt tccttgtcac tggtagacca | 2985 |
| aaataaaacc gactctactg gtcttgtgga attgggagct tgggaatgga tcctggagga | 3045 |
| tgcccaatta gggcctagcc ttaatcaggt cctcagagaa tttctaccat tcagagagg | 3105 |
| cctttttggaa tgtggcccct gaacaagaat tggaagctgc cctgcccatg ggagctggtt | 3165 |
| agaaatgcag aatcctaggc tccaccccat ccagttcatg agaatctata tttaacaaga | 3225 |
| tctgcagggg gtgtgtctgc tcagtaattt gaggacaacc attccagact gcttccaatt | 3285 |
| ttctggaata catgaaatat agatcagtta taagtagcag ccaagtcag gcccttattt | 3345 |
| tcaagaaact gaggaatttt ctttgtgtag ctttgctctt tggtagaaaa ggctaggtac | 3405 |
| acagctctag acactgccac acagggtctg caaggtcttt ggttcagcta agccggaatt | 3465 |
| c | 3466 |

<210> SEQ ID NO 5
<211> LENGTH: 575
<212> TYPE: PRT
<213> ORGANISM: homo sapiens

```
<400> SEQUENCE: 5

Met Leu Gly Val Leu Val Leu Gly Ala Leu Ala Leu Ala Gly Leu Gly
        -15                 -10                  -5

Phe Pro Ala Pro Ala Glu Pro Gln Pro Gly Gly Ser Gln Cys Val Glu
     -1   1               5                  10

His Asp Cys Phe Ala Leu Tyr Pro Gly Pro Ala Thr Phe Leu Asn Ala
 15              20                  25                      30

Ser Gln Ile Cys Asp Gly Leu Arg Gly His Leu Met Thr Val Arg Ser
             35                  40                  45

Ser Val Ala Ala Asp Val Ile Ser Leu Leu Asn Gly Asp Gly Gly
         50                  55                  60

Val Gly Arg Arg Arg Leu Trp Ile Gly Leu Gln Leu Pro Pro Gly Cys
         65              70                  75

Gly Asp Pro Lys Arg Leu Gly Pro Leu Arg Gly Phe Gln Trp Val Thr
         80              85                  90

Gly Asp Asn Asn Thr Ser Tyr Ser Arg Trp Ala Arg Leu Asp Leu Asn
 95                 100                 105                 110

Gly Ala Pro Leu Cys Gly Pro Leu Cys Val Ala Val Ser Ala Ala Glu
                115                 120                 125

Ala Thr Val Pro Ser Glu Pro Ile Trp Glu Glu Gln Cys Glu Val
             130                 135                 140

Lys Ala Asp Gly Phe Leu Cys Glu Phe His Phe Pro Ala Thr Cys Arg
             145                 150                 155

Pro Leu Ala Val Glu Pro Gly Ala Ala Ala Ala Val Ser Ile Thr
 160                 165                 170

Tyr Gly Thr Pro Phe Ala Ala Arg Gly Ala Asp Phe Gln Ala Leu Pro
 175                 180                 185                 190

Val Gly Ser Ser Ala Ala Val Ala Pro Leu Gly Leu Gln Leu Met Cys
                195                 200                 205

Thr Ala Pro Pro Gly Ala Val Gln Gly His Trp Ala Arg Glu Ala Pro
                 210                 215                 220

Gly Ala Trp Asp Cys Ser Val Glu Asn Gly Cys Glu His Ala Cys
             225                 230                 235

Asn Ala Ile Pro Gly Ala Pro Arg Cys Gln Cys Pro Ala Gly Ala Ala
 240                 245                 250

Leu Gln Ala Asp Gly Arg Ser Cys Thr Ala Ser Ala Thr Gln Ser Cys
 255                 260                 265                 270

Asn Asp Leu Cys Glu His Phe Cys Val Pro Asn Pro Asp Gln Pro Gly
                 275                 280                 285

Ser Tyr Ser Cys Met Cys Glu Thr Gly Tyr Arg Leu Ala Ala Asp Gln
                 290                 295                 300

His Arg Cys Glu Asp Val Asp Asp Cys Ile Leu Glu Pro Ser Pro Cys
             305                 310                 315

Pro Gln Arg Cys Val Asn Thr Gln Gly Gly Phe Glu Cys His Cys Tyr
 320                 325                 330

Pro Asn Tyr Asp Leu Val Asp Gly Glu Cys Val Glu Pro Val Asp Pro
 335                 340                 345                 350

Cys Phe Arg Ala Asn Cys Glu Tyr Gln Cys Gln Pro Leu Asn Gln Thr
                 355                 360                 365

Ser Tyr Leu Cys Val Cys Ala Glu Gly Phe Ala Pro Ile Pro His Glu
             370                 375                 380

Pro His Arg Cys Gln Met Phe Cys Asn Gln Thr Ala Cys Pro Ala Asp
 385                 390                 395
```

-continued

```
Cys Asp Pro Asn Thr Gln Ala Ser Cys Glu Cys Pro Glu Gly Tyr Ile
    400                 405             410
Leu Asp Asp Gly Phe Ile Cys Thr Asp Ile Asp Glu Cys Glu Asn Gly
415                 420             425                 430
Gly Phe Cys Ser Gly Val Cys His Asn Leu Pro Gly Thr Phe Glu Cys
            435             440                 445
Ile Cys Gly Pro Asp Ser Ala Leu Val Arg His Ile Gly Thr Asp Cys
            450             455             460
Asp Ser Gly Lys Val Asp Gly Gly Asp Ser Gly Ser Gly Glu Pro Pro
        465             470             475
Pro Ser Pro Thr Pro Gly Ser Thr Leu Thr Pro Pro Ala Val Gly Leu
    480             485             490
Val His Ser Gly Leu Leu Ile Gly Ile Ser Ile Ala Ser Leu Cys Leu
495             500             505             510
Val Val Ala Leu Leu Ala Leu Leu Cys His Leu Arg Lys Lys Gln Gly
            515             520             525
Ala Ala Arg Ala Lys Met Glu Tyr Lys Cys Ala Ala Pro Ser Lys Glu
            530             535             540
Val Val Leu Gln His Val Arg Thr Glu Arg Thr Pro Gln Arg Leu
            545             550             555
```